United States Patent
Jeppesen et al.

(10) Patent No.: US 12,188,070 B2
(45) Date of Patent: Jan. 7, 2025

(54) METHOD FOR PREPARING FERMENTABLE SUGARS FROM LIGNOCELLULOSIC BIOMASS

(71) Applicant: Inbicon A/S, Fredericia (DK)

(72) Inventors: Martin Dan Jeppesen, Odense (DK); Jan Larsen, Tommerup (DK); Kit Haubjerg Mogensen, Fredericia (DK); Anna Frederike Gossmann, Flensburg (DK); Anna Granly Hansen, Fredericia (DK); Laila Thirup, Skanderborg (DK); Lars Villadsgaard Toft, Silkeborg (DK); Hanne Risbjerg Sørensen, Holte (DK)

(73) Assignee: New Energy Blue LLC, Lancaster, PA (US)

( * ) Notice: Subject to any disclaimer, the term of this patent is extended or adjusted under 35 U.S.C. 154(b) by 0 days.

(21) Appl. No.: 16/347,091

(22) PCT Filed: Nov. 6, 2017

(86) PCT No.: PCT/EP2017/078340
§ 371 (c)(1),
(2) Date: May 2, 2019

(87) PCT Pub. No.: WO2018/083301
PCT Pub. Date: May 11, 2018

(65) Prior Publication Data
US 2019/0271017 A1 Sep. 5, 2019

Related U.S. Application Data

(60) Provisional application No. 62/417,570, filed on Nov. 4, 2016.

(51) Int. Cl.
| | | |
|---|---|---|
| *C12P 19/02* | (2006.01) | |
| *C07G 1/00* | (2011.01) | |
| *C08L 95/00* | (2006.01) | |
| *C12P 7/10* | (2006.01) | |
| *C12P 19/14* | (2006.01) | |
| *C13K 1/02* | (2006.01) | |
| *C13K 13/00* | (2006.01) | |

(52) U.S. Cl.
CPC ............... *C12P 19/02* (2013.01); *C07G 1/00* (2013.01); *C08L 95/00* (2013.01); *C12P 7/10* (2013.01); *C12P 19/14* (2013.01); *C13K 1/02* (2013.01); *C13K 13/002* (2013.01); *C12P 2201/00* (2013.01); *C12P 2203/00* (2013.01); *Y02E 50/10* (2013.01)

(58) Field of Classification Search
CPC ....... C12P 19/02; C12P 19/14; C12P 2201/00; C12P 7/10; C12P 2203/00; C12P 5/023; Y02E 50/10; Y02E 50/16; Y02E 50/30; Y02E 50/343; C13K 13/002; C13K 1/02; D21C 1/04; D21C 1/02; D21C 5/005; D21C 3/04; C07G 1/00; C08L 95/00
See application file for complete search history.

(56) References Cited

U.S. PATENT DOCUMENTS

| | | | |
|---|---|---|---|
| 9,920,345 B2* | 3/2018 | Larsen | C12P 7/10 |
| 2010/0068768 A1* | 3/2010 | Tolan | C12P 19/02 |
| | | | 435/99 |
| 2010/0279361 A1* | 11/2010 | South | A23K 20/163 |
| | | | 435/165 |
| 2013/0118483 A1 | 5/2013 | Gao et al. | |
| 2013/0236941 A1* | 9/2013 | Burns-Guydish | C12M 23/42 |
| | | | 435/165 |
| 2015/0191758 A1* | 7/2015 | Larsen | C13K 13/002 |
| | | | 435/99 |

FOREIGN PATENT DOCUMENTS

| | | | | |
|---|---|---|---|---|
| WO | WO 2011/028554 A1 | 3/2011 | | |
| WO | WO 2011/125056 A1 | 10/2011 | | |
| WO | WO-2013101650 A1 * | 7/2013 | | C12P 19/14 |
| WO | WO 2014/019589 A1 | 2/2014 | | |
| WO | WO 2014/026154 A1 | 2/2014 | | |
| WO | WO 2015/014364 A1 | 2/2015 | | |

OTHER PUBLICATIONS

Kowalski, K. "Recylcing the Dead", Science News for Students, pp. 1-12, Sep. 27, 2014. (Year: 2014).*

* cited by examiner

*Primary Examiner* — David W Berke-Schlessel
*Assistant Examiner* — Susan E. Fernandez
(74) *Attorney, Agent, or Firm* — Womble Bond Dickinson (US) LLP

(57) ABSTRACT

A method for providing a C5/C6 product from a lignocellulosic material is disclosed, said method comprising the steps: (i) pretreatment of the lignocellulosic material; (ii) solid/liquid separation of the pretreated lignocellulosic material from step (a) into a first solid fraction and a first liquid fraction; (iii) enzymatic fiber hydrolysis of said first solid fraction from step (b) by use of an enzyme composition capable of degrading lignocellulosic material, thereby providing a C5/C6 fiber slurry comprising C5 and/or C6 sugars; (iv) solid/liquid separation of the C5/C6 fiber slurry from step (c) into a second solid fraction and a second liquid fraction; and optionally (v) combining said first liquid fraction and said second liquid fraction for enzymatic mixed sugar hydrolysis (MSH), whereby a MSH C5/C6 product is provided.

18 Claims, 8 Drawing Sheets

Process scheme (2) - single step steam pretreatment, C5 bypass hydrolysis and post-hydrolysis Process scheme (3) - single step steam pretreatment, two step hydrolysis and mixed sugar hydrolysis

METHOD FOR PREPARING FERMENTABLE SUGARS FROM LIGNOCELLULOSIC BIOMASS

CROSS-REFERENCE TO RELATED APPLICATIONS

This application is a national stage filing under 35 U.S.C. 371 of PCT/EP2017/078340 filed Nov. 6, 2017, which International Application was published by the International Bureau in English on May 11, 2018, and application claims priority from U.S. Provisional Patent Application No. 62/417,570, filed Nov. 4, 2016, which applications are hereby incorporated in their entirety by reference in this application.

FIELD

The present invention relates to a method for processing lignocellulosic biomass to fermentable sugars, to a method for producing a fermentation product, such as by the use of a two-step fermentation method, and to a method for producing lignin.

BACKGROUND

Historical reliance on petroleum and other fossil fuels has been associated with dramatic and alarming increases in atmospheric levels of greenhouse gases. International efforts are underway to mitigate greenhouse gas accumulation, supported by formal policy directives in many countries. One central focus of these mitigation efforts has been the development of processes and technologies for utilization of renewable plant biomass to replace petroleum as a source of precursors for fuels and other chemical products.

Industrial manufacture of fuel ethanol from sugar and starch-based plant materials, such as sugarcane, root and grain crops, is already in wide global use. However, both environmental, economic and moral objections have been raised to these "first generation" bioethanol processes, e.g. for placing demand for crops as human food into direct competition with demand for fuel for personal automobiles.

Great interest has therefore arisen in developing biomass conversion systems that do not consume food crops-so-called "second generation" biorefining, whereby bioethanol and other products can be produced from lignocellulosic biomass such as crop wastes (stalks, cobs, pits, stems, shells, husks, etc.), grasses, straws, wood chips, waste paper and the like. In "second generation" technology, fermentable 6-carbon (C6) sugars derived primarily from cellulose and fermentable 5-carbon (C5) sugars derived from hemicellulose are liberated from biomass polysaccharide polymer chains by enzymatic hydrolysis or, in some cases, by pure chemical hydrolysis. The fermentable sugars obtained from biomass conversion in a "second generation" biorefinery can be used to produce e.g. ethanol, acetone, butanol, lactic acid, and/or other compounds useful as e.g. fuel or precursors for chemical products, e.g. various polymers etc.

The total yield of both C5 and C6 sugars is a key factor in the economic viability of commercialization of lignocellulosic biomass processing. Because of limitations of its physical structure, lignocellulosic biomass cannot be effectively converted to fermentable sugars by enzymatic hydrolysis without some pretreatment process. A wide variety of different pretreatment schemes have been reported, each offering different advantages and disadvantages.

WO2014/019589, herewith incorporated by reference in its entirety, discloses a method for processing of lignocellulosic biomass comprising a pretreatment and enzymatic processing of a solid fraction to produce a C5/C6 product.

WO2015/014364, herewith incorporated by reference in its entirety, discloses a method for processing lignocellulosic biomass using a single-stage autohydrolysis pretreatment and enzymatic hydrolysis.

SUMMARY OF THE INVENTION

Figure 1:
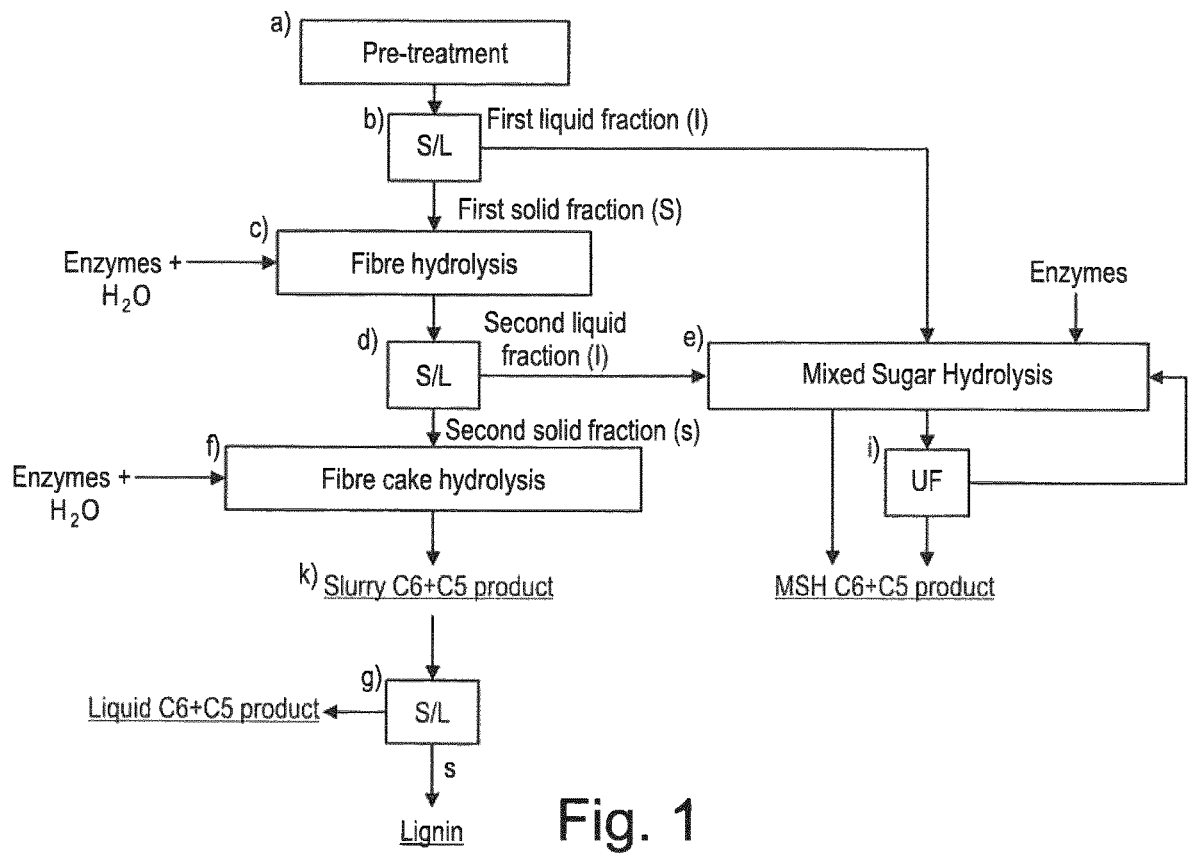
FIG. 1: Schematic outline of process steps pertaining to methods according to the present invention.

In a first aspect, the current invention pertains to a method for providing a C5/C6 product from a lignocellulosic material comprising the steps:
 a) Pretreatment of the lignocellulosic material;
 b) Solid/liquid separation of the pretreated lignocellulosic material from step (a) into a first solid fraction and a first liquid fraction;
 c) Enzymatic fiber hydrolysis of said first solid fraction from step (b) by use of an enzyme composition capable of degrading lignocellulosic material, thereby providing a C5/C6 fiber slurry comprising C5 and/or C6 sugars;
 d) Solid/liquid separation of the C5/C6 fiber slurry from step (c) into a second solid fraction and a second liquid fraction; and optionally
 e) Combining said first liquid fraction and said second liquid fraction for enzymatic Mixed sugar hydrolysis (MSH), whereby a MSH C5/C6 product is provided.

In a second aspect, the current invention relates to a method for providing a fermentation product, said method comprising the steps of:
 m) Providing at least one C5/C6 product according to the method of any one of the preceding embodiments; and
 n) Providing the fermentation product by a fermentation of said C5/C6 product with a microorganism.

In a third aspect, the current invention concerns a two-step fermentation method comprising the steps of:
 aa) Pretreatment of the lignocellulosic material;
 bb) Solid/liquid separation of the pretreated lignocellulosic material from step (aa) into a first solid fraction and a first liquid fraction;
 cc) Enzymatic fiber hydrolysis of said first solid fraction from step (bb) by use of an enzyme composition capable of degrading lignocellulosic material, thereby providing a C5/C6 fiber slurry;
 dd) Solid/liquid separation of the C5/C6 fiber slurry from step (cc) into a second solid fraction and a second liquid fraction;
 ee) Enzymatic mixed sugar hydrolysis (MSH) of a mixture of the first liquid fraction from step (bb) and the C5/C6 fiber slurry from step (cc), or the first liquid fraction from step (bb) and the second liquid fraction from step (dd), thereby providing a C5/C6 MSH product;
 ff) Providing a first fermentation substrate comprising at least a portion of the "C5/C6 fiber hydrolysis slurry" and/or the second liquid fraction;
 gg) Providing a second fermentation substrate comprising at least a portion of the C5/C6 MSH product;
 hh) Fermenting the first fermentation substrate in a first fermentation with a microorganism; and
 ii) Fermenting the second fermentation substrate in a subsequent second fermentation;
 wherein step (dd) is optional.

In a fourth aspect, the current invention concerns a method for preparing ethanol and lignin from a lignocellulosic material comprising the steps of:
 Providing at least one C5/C6 product according to a method according to any one of the preceding aspects;
 Fermentation of said at least one C5/C6 product to convert sugars to ethanol in the fermentation broth with a yeast;
 Isolation of an ethanol rich fraction from the fermentation broth; and optionally
 Isolation of lignin.

In a fifth aspect, the current invention pertains to lignin provided from lignocellulosic biomass according to any one of the preceding aspects.

In a sixth aspect, the current invention relates to a C5/C6 product provided according to any one of the preceding aspects.

In a seventh aspect, the current invention concerns a fermentation substrate comprising a C5/C6 product provided by a method according to any one of the preceding aspects.

In an eighth aspect, the current invention pertains to a first or second fermentation substrate provided by a method according to any one of the preceding aspects.

In a ninth aspect, the current invention relates to compositions comprising lignin obtained or obtainable by a method according to any of the previous aspects, including different uses of said lignin-comprising compositions.

DETAILED DESCRIPTION

Methods for preparing hydrolysed lignocellulosic biomass which can be fermented by microorganisms to yield small organic molecules are only suited for large-scale industrial use if such methods are economically competitive methods. In order to be economically competitive such methods must exhibit high yield of C6 sugars and/or C5 sugars, as low as possible consumption of energy, enzymes and other prerequisites on the cost-side as well as preferably provide by-products having a significant value.

The present inventors have surprisingly found a method for preparing a C5/C6 and/or a C6+C5 product from a lignocellulosic material which exhibit relatively low energy input, fast and efficient hydrolysis of the lignocellulosic material to C6 and/or C5 sugars, while at the same time providing a substantial amount of high-value lignin as a by-product.

The particular advantage of the present invention is that separate hydrolysis of liquid and solid fractions of pretreated lignocellulosic biomass produces at least two C5/C6 and/or C6+C5 product fraction, one e.g. having mainly C6 sugars and low concentration of fermentation inhibitory substances and one e.g. having mainly C5 sugars and higher amount of fermentation inhibitory substances. Hence, fermentation of the C5/C6 and/or C6+C5 products may advantageously be carried out by first fermenting the low inhibitor fraction and then subsequently adding and fermenting the high inhibitor fraction.

In some embodiments, the present invention relates to a method for preparing at least one C5/C6 product, such as a C6 and/or C5 sugar, from a lignocellulosic material comprising the steps:
 I. Pretreatment of the lignocellulosic material,
 II. Solid/liquid separation into a first solid fraction and a first liquid fraction,
 III. Enzymatic hydrolysis of said first solid fraction from step II) by use of an enzyme composition comprising at least one cellulase and/or hemicellulase (such as a xylanase),
 IV. Solid/liquid separation of the reaction mixture from step III) into a second solid fraction and a second liquid fraction, and optionally
 V. Mixing of said first liquid fraction and said second liquid fraction for enzymatic hydrolysis to obtain a C5/C6 product, and optionally VI. Recycling enzymes present after enzymatic hydrolysis in step III).

FIG. 1 shows different embodiments of the invention, in particular a method for providing a C5/C6 product from a lignocellulosic material comprising the steps:
a) Pretreatment of the lignocellulosic material;
b) Solid/liquid separation of the pretreated lignocellulosic material from step (a) into a first solid fraction and a first liquid fraction;
c) Enzymatic fiber hydrolysis of said first solid fraction from step (b) by use of an enzyme composition capable of degrading lignocellulosic material, thereby providing a C5/C6 fiber hydrolysis slurry comprising C5 and/or C6 sugars;
d) Solid/liquid separation of the C5/C6 fiber slurry from step (c) into a second solid fraction and a second liquid fraction; and optionally
e) Combining said first liquid fraction and said second liquid fraction for enzymatic Mixed sugar hydrolysis (MSH), whereby a MSH C5/C6 product is provided; and optionally
f) Enzymatic fiber cake hydrolysis of said second solid fraction from step (d) to obtain a slurry C5/C6 product; and optionally
g) Solid/liquid separation of the slurry C5/C6 product from step (f) into a third solid fraction and a liquid C5/C6 product; and optionally
h) Combining at least a portion of the MSH C5/C6 product with at least a portion of one or more of: the slurry C5/C6 product from step (f), the liquid C5/C6 product from step (g), and/or the second liquid fraction from step (d) to obtain a combined C5/C6 product; and optionally
i) Ultrafiltration step for recycling enzymes present after the MSH in step (e).

The liquid fraction provided by the solid/liquid separations of steps b) and d) can be maintained separately from the solid fractions during enzymatic hydrolysis, c.f. FIG. 1. Separate enzymatic hydrolysis of the solid fractions may take place in the fiber hydrolysis in step c) and the fiber cake hydrolysis in step f), thus providing advantages of the current invention in comparison to the prior art, such as a higher yield of C6 and C5 sugars from the solid fraction and leaving the slurry C6+C5 product rich in high-value lignin in the solid part. Usually, the liquid fractions obtained in solid/liquid separation steps b) and d) can be combined and subjected to a mixed sugar hydrolysis (MSH), such as disclosed in step e), c.f. FIG. 1.

As used herein, the following terms have the following meaning:

The terms "C5/C6 product" and/or "C6/C5 product" can be used interchangeably, and is/are meant to comprise a composition comprising at least one C6 sugar and/or at least one C5 sugar, where C6 sugar and C5 sugar may be any carbohydrate having six or five carbon atoms, respectively.

The terms "C6+C5 product" and/or "C6/C5 product" can be used interchangeably, and is/are meant to comprise a composition comprising at least one C6 sugar and at least one C5 sugar, where C6 sugar and C5 sugar may be any carbohydrate having six or five carbon atoms, respectively.

The C5/C6 and/or C6+C5 product may be a liquid, a suspension or slurry, or a solid composition and it may contain additional compounds in addition to the C6 sugar and/or C5 sugar, such as compounds originating from a degradation process to liberate the C6 and C5 sugars from macromolecules. Such additional compounds may e.g. be poly-, oligo- or disaccharides, furfural, salts etc., but also lignin, and/or lignin-derived compounds and/or compositions.

Non-limiting examples of C6 sugar are e.g. glucose, galactose, mannose, rhamnose and the like. Non-limiting examples of C5 sugar are xylose, arabinose etc. When a C6+C5 product is obtained by hydrolysis of lignocellulosic material the C6 sugar glucose is primarily obtained from the cellulose part whereas C5 sugar, mannose, galactose and rhamnose are primarily obtained from the hemicellulose part of the lignocellulosic material. Said C5 and/or C6 sugar(s) may be modified, such as esterified or the like.

In some embodiments, the C6 sugar is fermentable C6 sugar, e.g. carbohydrates having six carbon atoms and which can be fermented by well-known microorganisms, such as naturally occurring microorganisms or genetically modified microorganisms.

In some embodiments, the C5 sugar is fermentable C5 sugar, e.g. carbohydrates having five carbon atoms and which can be fermented by well-known microorganisms such as naturally occurring microorganisms or genetically modified microorganisms.

The term "C1-C4 product" as used herein means a small molecular weight organic compound having from one to four carbon atoms. Non-limiting examples of C1-C4 products are methanol, ethanol, butanol, acetone, formic acid, acetic acid, propionic acid, butyric acid, oxalic acid, lactic acid, malic aid, and/or any combination thereof.

The term "Fermentation product" may comprise a C1-C4 product, as in the context of the current invention, the term "fermentation product(s)" is meant to comprise any product that can be provided by fermentation with one or more microorganism(s). Fermentations according to the invention may comprise aerobic or anaerobic fermentations, e.g. fermentations when pyruvate is reduced to fermentation products such as ethanol, lactic acid, 3 hydroxy-propionic acid, acrylic acid, acetic acid, succinic acid, citric acid, malic acid, fumaric acid, an amino acid, 1,3-propane-diol, ethylene, glycerol, butanol, a P-lactam antibiotic and a cephalosporin. A "Fermentation product" may also comprise value-added products including, but not limited to one or more of: biofuels (including methanol, ethanol, propanol and butanol); alcohol, aldehyde, ketone, lactic acid; 3-hydroxy-propionic acid; acrylic acid; acetic acid; 1,3-propane-diol; ethylene; glycerol; a plastic; a specialty chemical; an organic acid, including citric acid, succinic acid and maleic acid; a solvent; an animal feed supplement; a pharmaceutical such as a p-lactam antibiotic or a cephalosporin; a vitamin; an amino acid, such as lysine, methionine, tryptophan, threonine, and aspartic acid; a peptide, a protein, an enzyme, such as a protease, a cellulase, a hemicellulase, a xylanase, an amylase, a glucanase, a lactase, a lipase, a lyase, an oxidoreductase, an esterase, or a transferase; a chemical feedstock; or an animal feed supplement.

"About" as used herein, usually with reference to a quantitative number or range, may refer to +/−1, 2, 5 or even 10% in relative terms of the number or range referred to.

"Autohydrolysis" refers to a pretreatment process of lignocellulosic biomass, in which acetic acid is liberated from hemicellulose during said process, which is believed to further catalyse and/or improve hemicellulose hydrolysis. Autohydrolysis of lignocellulosic biomass is thus conducted without or essentially without addition of any further chemicals, such as acid(s) or base(s), and is commonly performed at a pH between 3.5 and 9.0.

"Commercially available cellulase preparation optimized for lignocellulosic biomass conversion" refers to a commercially available mixture of enzyme activities which is sufficient to provide enzymatic hydrolysis of pretreated lignocellulosic biomass and which usually comprises endocellulase (endoglucanase), exocellulase (exoglucanase), endoxylanase, acetyl xylan esterase, xylosidase and β-glucosidase activities. The term "optimized for lignocellulosic biomass conversion" refers to a product development process in which enzyme mixtures have been selected and/or modified for the specific purpose of improving hydrolysis yields and/or reducing enzyme consumption in hydrolysis of pretreated lignocellulosic biomass to fermentable sugars.

The term "Cellulase(s)" is meant to comprise one or more enzymes capable of degrading cellulose and/or related compounds. Cellulase is any of several enzymes commonly produced by fungi, bacteria, and protozoans that catalyse cellulolysis, the decomposition of cellulose and/or related polysaccharides. Cellulase can also be used for any mixture or complex of various such enzymes, that act serially or synergistically to decompose cellulosic material. Cellulases break down the cellulose molecule into monosaccharides ("simple sugars") such as beta-glucose, and/or shorter polysaccharides and oligosaccharides. Specific reactions may comprise hydrolysis of the 1,4-beta-D-glycosidic linkages in cellulose, hemicellulose, lichenin, and cereal beta-D-glucans. Several different kinds of cellulases are known, which differ structurally and mechanistically. Synonyms, derivatives, and/or specific enzymes associated with the name "cellulase" comprise endo-1,4-beta-D-glucanase (beta-1,4-glucanase, beta-1,4-endoglucan hydrolase, endoglucanase D, 1,4-(1,3,1,4)-beta-D-glucan 4-glucanohydrolase), carboxymethyl cellulose (CMCase), avicelase, celludextrinase, cellulase A, cellulosin AP, alkali cellulase, cellulase A 3, 9.5 cellulase, and pancellase SS.

Cellulases can also be classified based on the type of reaction catalysed, where endocellulases (EC 3.2.1.4) randomly cleave internal bonds at amorphous sites that create new chain ends, exocellulases or cellobiohydrolases (EC 3.2.1.91) cleave two to four units from the ends of the exposed chains produced by endocellulase, resulting in tetra-, tri- or disaccharides, such as cellobiose. Exocellulases are further classified into type I—that work processively from the reducing end of the cellulose chain, and type II—that work processively from the nonreducing end. Cellobiases (EC 3.2.1.21) or beta-glucosidases hydrolyse the exocellulase product into individual monosaccharides. Oxidative cellulases depolymerize cellulose by radical reactions, as for instance cellobiose dehydrogenase (acceptor). Cellulose phosphorylases depolymerize cellulose using phosphates instead of water.

The term "Hemicellulase(s)" is meant to comprise one or more enzymes capable and/or contributing to breaking down hemicellulose, one of the major components of plant cell walls. Some of the main polysaccharides that constitute hemicellulose are believed to be xylan, arabinoxylan, xyloglucan, glucuronoxylan and glucomannan. In the context of the present invention, the term "hemicellulase(s)" is meant to comprise: xylanase(s), xylosidase(s), arabinoxylanase(s), xyloglucanase(s), glucoronoxylanase(s), glucomannanase(s), and/or esterase(s), including any combination thereof.

The term "Xylanase(s)" is meant to comprise one or more enzymes capable of degrading xylan and/or related compounds. Xylanase is any of several enzymes produced e.g. by microorganisms such as yeast that catalyse decomposition of xylan and/or related polysaccharides. Xylanase can also be used for any mixture or complex of various such enzymes that act serially or synergistically to decompose xylanosic material. Synonyms, derivatives, and specific enzymes associated with the name "xylanase" may comprise EC 3.2.1.8, endo-(1→4)-beta-xylan 4-xylanohydrolase, endo-1,4-xylanase, endo-1,4-beta-xylanase, beta-1,4-xylanase, endo-1,4-beta-D-xylanase, 1,4-beta-xylan xylanohydrolase, beta-xylanase, beta-1,4-xylan xylanohydrolase, beta-D-xylanase and/or xylosidase capable of degrading xylan, such as beta-1,4-xylan into xylose, thus contributing to breaking down hemicellulose, one of the major components of plant cell walls.

"Xylosidase" as used herein is intended to comprise the enzyme xylan 1,4-beta-xylosidase (E.C. 3.2.1.37) which is also named xylobiase, beta-xylosidase, exo-1,4-beta-D-xylosidase or 4-beta-D-xylan xylohydrolase. This enzyme catalyses the hydrolysis of (1-4)-beta-D-xylans removing successive D-xylose residues from the non-reducing termini of the substrate, e.g. hemicellulose and the disaccharide xylobiose. This enzyme is believed to be commercially available both as an essentially pure xylosidase enzyme or e.g. as a part of cellulase preparations.

The term "Arabinoxylanase(s)" is meant to comprise one or more enzymes capable of degrading arabinoxylan and/or related compounds, comprising e.g. glucuronoarabinoxylan endo-1,4-beta-xylanase (EC 3.2.1.136), feraxan endoxylanase, feraxanase, endoarabinoxylanase, glucuronoxylan xylohydrolase, glucuronoxylanase, glucuronoxylan xylanohydrolase, glucuronoarabinoxylan 1,4-beta-D-xylanohydrolase), and glucuronoarabinoxylan 4-beta-D-xylanohydrolase. Glucuronoarabinoxylan 4-beta-D-xylanohydrolase is believed to endohydrolyse (1→4)-beta-D-xylosyl links in some glucuronoarabinoxylans. It also believed that this enzyme possesses a high activity towards feruloylated arabinoxylans. (Nishitani, K.; Nevins, D. J. (1988). "Enzymic analysis of feruloylated arabinoxylans (Feraxan) derived from *Zea mays* cell walls. I. Purification of novel enzymes capable of dissociating Feraxan fragments from *Zea mays* coleoptile cell wall". Plant Physiol. 87:883-890.)

The term "Xyloglucanase(s)" is meant to comprise one or more enzymes capable of degrading xyloglucan and/or related compounds, comprising e.g. xyloglucan-specific endo-beta-1,4-glucanase (EC 3.2.1.151), which is an enzyme that is believed to catalyse the chemical reaction: xyloglucan+H2O→xyloglucan oligosaccharides. This enzyme belongs to the family of hydrolases, specifically those glycosidases that hydrolyse O- and S-glycosyl compounds. The systematic name of this enzyme class is [(1→6)-alpha-D-xylo]-(1→4)-beta-D-glucan glucanohydrolase. Other names in common use may include XEG, xyloglucan endo-beta-1,4-glucanase, xyloglucanase, xyloglucanendohydrolase, XH, and 1,4-beta-D-glucan glucanohydrolase.

The term "Glucuronoxylanase(s)" is meant to comprise one or more enzymes capable of degrading glucuronoxylan and/or related compounds.

The term "Glucomannanase(s)" is meant to comprise one or more enzymes capable of degrading glucomannanase and/or related compounds.

The term "Esterase(s)" is meant to comprise one or more enzymes capable of splitting an ester in an acid and an alcohol. Examples of esterases comprise acetylesterases and feroyl esterase.

The term "Acetylesterase(s)" is meant to comprise an enzyme capable of splitting off acetyl groups. An acetylesterase (EC 3.1.1.6) is an enzyme that catalyses the chemical reaction: acetic ester+H2O→alcohol+acetate. This enzyme belongs to the family of hydrolases, specifically those acting on carboxylic ester bonds. The systematic name of this enzyme class is acetic-ester acetylhydrolase. Other names in common use include C-esterase (in animal tissues), acetic ester hydrolase, chloroesterase, p-nitrophenyl acetate esterase, and Citrus acetylesterase.

The terms "Feroyl esterase(s)" and "Feruloyl esterase(s)" can be used interchangeably, and is/are meant to comprise an enzyme that catalyses the chemical reaction feruloyl-(poly-, oligo-, or mono-)polysaccharide+H2O→ferulic acid+ (poly-, oligo-, or mono-) saccharide. Feroyl esterase belongs to the family of hydrolases, specifically those acting on carboxylic ester bonds. The systematic name of this enzyme class is feruloyl esterase (EC 3.1.1.73); other names may include ferulic acid esterase (FAE), hydroxycinnamoyl esterase, hemicellulase accessory enzyme, and cinnamoyl ester hydrolase (cinnAE).

Suitable microbial enzymes, such as cellulases, hemicellulase(s) including xylanases, and or esterases, can be expressed in suitable hosts using methods known in the art. Such enzymes are also commercially available, either in pure form or in enzyme cocktails. Specific enzyme activities can be purified from commercially available enzyme cocktails, again using methods known in the art—see e.g. Sørensen et al. (2005) "Efficiencies of designed enzyme combinations in releasing arabinose and xylose from wheat arabinoxylan in an industrial fermentation residue" (Enzyme and Microbial Technology 36 (2005) 773-784), where a *Trichoderma reesei* beta-xylosidase is purified from Celluclast (Finizym), and further commercial enzyme preparations are disclosed.

Conducting a treatment/process, such as a pretreatment "at" a dry matter level refers to the dry matter content of the feedstock at the start of said treatment. Likewise, conducting a treatment/process, such as a pretreatment "at" a pH refers to the pH of the aqueous content of the biomass at the start of said treatment.

In the context of the present invention, the term "pH- and temperature-adjusted" is meant to comprise pH and/or temperature adjustments in order to allow an enzymatic hydrolysis and/or fermentation to take place under suitable pH and/or temperature conditions.

"Dry matter," also appearing as "DM", refers to total solids, both soluble and insoluble, and effectively means "non-water content." Dry matter content is measured by drying at 105° C. until constant weight is achieved. "Fiber structure" is maintained to the extent that the average size of fiber fragments following pretreatment is >750 μm.

"Hydrothermal pretreatment" or sometimes only "pretreatment" commonly refers to the use of water, either as hot liquid, vapour steam or pressurized steam comprising high temperature liquid or steam or both, to "cook" biomass, at temperatures of 120° C. or higher, either with or without addition of acids or other chemicals. In the context of the present invention, "hydrothermal pretreatment" is meant to comprise methods, unit operations and/or processes relating to softening lignocellulosic biomass by the use of temperature and water, and usually, also, pressure, aiming at providing a pretreated biomass suitable for enzymatic digestion.

"Single-stage pressurized hydrothermal pretreatment" refers to a pretreatment in which biomass is subject to pressurized hydrothermal pretreatment in a single reactor configured to heat biomass in a single pass and in which no further pressurized hydrothermal pretreatment is applied following a solid/liquid separation step to remove liquid fraction from feedstock subject to pressurized hydrothermal pretreatment.

"Process" water refers to water of a quality suitable for the intended use in an industrial process. Commonly, process water is of lower quality than e.g. drinking water. Process water may comprise water that is recycled from an industrial process, such as a process according to the present invention. Process water may be adjusted in terms of mineral/salt content, pH and the like.

"Solid/liquid separation" refers to an active mechanical process, and/or unit operation(s), whereby liquid is separated from solid by application of force through e.g. pressing, centrifugation, sedimentation, decanting or the like. Commonly, a solid/liquid (s/l) separation provides a liquid and solid fraction.

"Solid fraction" and "Liquid fraction" refer to fractionation of pretreated and/or hydrolysed biomass in solid/liquid separation. The separated liquid is collectively referred to as "liquid fraction." The residual fraction comprising considerable insoluble solid content is referred to as "solid fraction". A "solid fraction" will have a substantial dry matter content and typically will also comprise a considerable residual of "liquid fraction" thus having the form of a solid or a slurry.

"Lignocellulosic biomass" refers to plant biomass comprising cellulose and lignin, and usually also hemicellulose.

"Soft lignocellulosic biomass" refers to plant biomass other than wood, which comprises cellulose and lignin, and usually also hemicellulose.

The term "lignin" is meant to comprise a complex phenolic polymer, which forms an integral part of the secondary cell walls of various plants. It is believed that lignin is one of the most abundant organic polymers on earth, exceeded only by cellulose, and constituting from 25 to 33% of the dry mass of wood and 20 to 25% for annual crops. "Lignin" is also used for a lignin component obtained in the biomass refining process, usually comprising pretreatment. Thus, the term "lignin" in the present description and in the appended claims refers to the polymer denoted as such and being present in unprocessed lignocellulosic plant material, as well as "lignin" that has been subject to various physical and/or chemical treatments, usually imposing only minor changes of the lignin polymer structure, such as maintaining its polymer character. Examples for such physical and/or chemical treatments comprise processes and methods for providing a C5/C6 product as disclosed herein. "Lignin" may comprise significant amounts of hemicellulose and cellulose and/or other sugars. Hence "lignin" as used in the present description and in the appended claims may refer to a lignin that has been subjected to slight structural modifications and/or comprising some amount of chemical residues originating from its mode of manufacture, or originating from compounds native for the lignocellulosic material from which it is isolated.

In the context of the present invention, the term "inhibitor" is meant to comprise one or more components or chemicals reducing (i) the effectiveness of process, such as a chemical reaction, e.g. catalysed by a catalyst such as an enzyme; (ii) growth of a microorganism; and/or (iii) reducing metabolism, in particular product yield, such as reduction in product yield of a fermentation product. "Fermentation inhibitors" are inhibitors of type (ii) and/or (iii). At least three categories of fermentation inhibitors are typically formed during autohydrolysis pretreatment: (1) furans, primarily 2-furfural and 5 hydroxymethylfurfural (5-HMF) which are degradation products from mono- or oligo-saccharides; (2) monomeric phenols, which are degradation products of the lignin structure; and (3) small organic acids, primarily acetic acid, which originate from acetyl groups in hemicellulose and lignin. Further details concerning inhibitors found in pretreated biomass, and methods of their determination and analysis can e.g. be found in Rasmussen (2016) "Carbohydrate degradation mechanisms and compounds from pretreated biomass" PHD Thesis, Technical University of Denmark.

"Theoretical yield" refers to the molar equivalent mass of pure monomer sugars obtained from polymeric cellulose, or from polymeric hemicellulose structures, in which constituent monomeric sugars may also be esterified or otherwise substituted. "C5 monomer yields" as a percentage of theoretical yield are determined as follows: Prior to pretreatment, biomass feedstock is analysed for carbohydrates using strong acid hydrolysis and an HPLC system in which galactose and mannose co-elute with xylose. Examples of such systems are REZEX™, Monossacharide H+ column from Phenomenex and an AMINEX HPX 87C™ column from Biorad. During strong acid hydrolysis, esters and acid-labile substitutions are removed. Except as otherwise specified, the total quantity of "Xylose"+Arabinose determined in the un-pretreated biomass is taken as a 100% theoretical C5 monomer recovery, which can be termed collectively "C5 monomer recovery". Monomer sugar determinations are made using HPLC characterization based on standard curves with purified external standards. Actual C5 monomer recovery is determined by HPLC characterization of samples for direct measurement of C5 monomers, which are then expressed as a percent of theoretical yield. "Xylan number" refers to a characterization of pretreated biomass determined as follows: Pretreated biomass is subject to solid/liquid separation to provide a solid fraction at about 30% total solids and a liquid fraction. This solid fraction is then partially washed by mixing with 70° C. water in the ratio of total solids (DM) to water of 1:3 wt:wt. The solid fraction washed in this manner is then pressed to about 30% total solids. Alternatively, the pretreated biomass can be subjected to solid/liquid separation to provide a solid fraction at about 50% total solids and a liquid fraction. With both methods, about 25% of the dissolved solids remain in the solid fraction with the suspended solids. Xylan content of the solid fraction washed in this manner can determined using e.g. the method of A. Sluiter, et al., "Determination of structural carbohydrates and lignin in biomass," US National Renewable Energy Laboratory (NREL) Laboratory Analytical Procedure (LAP) with issue date Apr. 25, 2008, as described in Technical Report NREL/TP-510-42618, revised April 2008, which is expressly incorporated by reference herein in entirety. This measurement of xylan content as described will include some contribution of soluble material from residual liquid fraction that is not washed out of solid fraction under these conditions. Accordingly, in the context of the present invention, the term "xylan number(s)" relates to (pre) treatment severities and relates to a composite measurement and/or values that reflect a weighted combination of both residual xylan content remaining within insoluble solids and also the concentration of soluble xylose and xylo-oligomers within the liquid fraction. At lower Ro severity, xylan numbers are higher. Thus, the highest xylan number refers to the lowest pretreatment severity. Xylan numbers provide a negative linear correlation with the conventional severity measure log $R_0$ even to low severity, where residual xylan content within insoluble solids is above 10%. Generally, low, medium and high pretreatment severities provide xylan numbers of >10%, 6-10%, and <6%, respectively.

In the context of the present invention, unless indicated otherwise, "%" indicates % weight/weight (w/w).

In the context of the present invention, the terms "about", "around", "approximately" or the symbol "~" can be used interchangeably, and are meant to comprise variations generally accepted in the field, e.g. comprising analytical errors and the like. Thus "about" may also indicate measuring uncertainty commonly experienced in the art, which can be in the order of magnitude of e.g. +/−1, 2, 5, 10, 20, or even 50 percent.

The term "comprising" is to be interpreted as specifying the presence of the stated parts, steps, features, components, or the like, but does not exclude the presence of one or more additional parts, steps, features, components etc. For example, a composition comprising a chemical compound may thus comprise additional chemical compounds.

A "derivative" is a compound that is derived from a similar compound by a chemical reaction.

An "isomer" is a molecule with the same molecular formula as another molecule, but with a different chemical structure. That is, isomers contain the same number of atoms of each element, but have different arrangements of their atoms. Isomers do not necessarily share similar properties, unless they also have the same functional groups. There are two main forms of isomerism: structural isomerism (or constitutional isomerism) and stereoisomerism (or spatial isomerism).

A "structural analogue", also known as a chemical analogue or simply an analogue, is a compound having a structure similar to that of another one, but differing from it in respect of a certain component.

It can differ in one or more atoms, functional groups, or substructures, which are replaced with other atoms, groups, or substructures. A structural analogue can be imagined to be formed, at least theoretically, from the other compound.

In the context of the present invention, terms related to "recovering", "isolating", "purifying" and "concentrating" may be used interchangeable, and are meant to comprise processes and/or unit operations aiming at providing a desired product, compound, and the like, such as a fermentation product or lignin in a more concentrated, less contaminated and/or purer form. Suitable processes, operations and/or processes are believed to be well known in the art.

Lignocellulosic biomass comprises crystalline cellulose fibrils intercalated within a loosely organized matrix of hemicellulose and sealed within an environment rich in hydrophobic lignin. While cellulose itself comprises long, straight chain polymers of D-glucose, hemicellulose is a heterogeneous mixture of short, branched-chain carbohydrates including monomers of all the 5-carbon aldopentoses (C5 sugars) as well as some 6-carbon (C6) sugars including glucose and mannose. Lignin is a highly heterogeneous polymer, lacking any particular primary structure, and comprising hydrophobic phenylpropanoid monomers. Suitable lignocellulosic biomass typically comprises cellulose in amounts between 20 and 50% of dry mass prior to pretreatment, lignin in amounts between 10 and 40% of dry mass prior to pretreatment, and hemicellulose in amounts between 15 and 40%.

In some embodiments, biomass feedstocks may be subject to particle size reduction and/or other mechanical processing such as grinding, chopping, milling, shredding, cutting or other processes prior to hydrothermal pretreatment. Other mechanical treatments may comprise cleaning/purification means, such as means for removing non-biomass components or objects, such as stones, grabble, sand, dust, and/or foreign objects such as metal or plastic objects and the like.

In some embodiments, biomass feedstocks may be washed and/or leached of valuable salts prior to pressurized pretreatment. In some embodiments, feedstocks may be soaked prior to pressurized pretreatment at temperatures up to 99° C. Said washing and/or leaching is usually conducted at around environmental pressure.

In some embodiments, the feedstock is first soaked in an aqueous solution prior to hydrothermal pretreatment. In some embodiments, the feedstock is soaked in an acetic acid containing liquid obtained from a subsequent step in the pretreatments, as described in U.S. Pat. No. 8,123,864, which is hereby incorporated by reference in entirety. It may be advantageous to conduct treatment at the highest possible dry matter content, as described in U.S. Ser. No. 12/935,587, which is hereby incorporated by reference in entirety. Conducting pretreatment at high dry matter avoids expenditure of process energy on heating of unnecessary water. However, some water content is required to achieve optimal sugar yields from enzymatic hydrolysis. Typically, it is advantageous to pretreat biomass feedstocks at or close to their inherent water holding capacity. This is the level of water content that a given feedstock will attain after soaking in an excess of water followed by pressing to the mechanical limits of an ordinary commercial screw press (typically between 30 and 45% DM). In some embodiments, hydrothermal pretreatment is conducted at a DM content of at least 35%. It will be readily understood by one skilled in the art that the DM content may decrease during hydrothermal pretreatment as some water content is added during heating. In some embodiments, feedstocks are pretreated at a DM content of at least 20%, or at least 25%, or at least 30%, or at least 40%, or at less than 40%, or at less than 35%, or at less than 30%. Further suitable DM contents may be described elsewhere herein.

In some embodiments, soaking/wetting with an aqueous solution can serve to adjust pH prior to pretreatment to the range of between 3.5 and 9.0, which is typically advantageous for autohydrolysis. It will be readily understood that pH may change during pretreatment, typically to more acidic levels as acetic acid is liberated from solubilized hemicellulose. Further suitable pH values may be disclosed elsewhere herein.

Xylan number is particularly useful as a measure of pretreatment severity in that different pretreated biomass feedstocks having equivalent xylan number exhibit equivalent C5 monomer recovery. In contrast, conventional $R_0$ severity is simply an empirical description of pretreatment conditions, which does not provide a rational basis for comparisons between different biomass feedstocks. For example, single-stage autohydrolysis to severity log $R_0$=3.75 provides pretreated sugar cane bagasse and corn stover having a xylan number of between 6-7%, while with typical wheat straw varieties, the resulting xylan number of pretreated feedstock is about 10%.

It may be advantageous that biomass feedstocks be pretreated to low severity wherein xylan number of the pretreated feedstock is greater 10% or greater. This low severity level corresponds to a process in which the total hemicellulose content of the feedstock before pretreatment that is either solubilized or irretrievably lost during pretreatment is minimized. At xylan number 10% and higher, with typical strains of wheat straw, sugar cane bagasse, sweet sorghum bagasse, corn stover, and empty fruit bunches (from oil palm), at least 60% of the original C5 content of the feedstock can be recovered after single-stage autohydrolysis pretreatment, where both xylan in the solid fraction and also soluble xylose and xylo-oligomers in the liquid fraction are accounted for. High final C5 monomer yields of at least 55% theoretical, or at least 60%, or at least 65%, can be obtained without appreciable loss of C6 monomer yields after enzymatic hydrolysis of feedstocks pretreated to very low severity by single-stage autohydrolysis. At very low severity levels, a large fraction of the feedstock's hemicellulose content remains within the solid fraction after pretreatment, where it can subsequently be hydrolysed to C5 monomers with high recovery using enzymatic hydrolysis.

It should be noted that reports concerning "xylose recovery" are often expressed in terms that may not be directly comparable to the xylose recoveries reported here. For example, reported xylose recoveries often refer only to xylose recovery from pretreated biomass, not expressed as a percentage of the original hemicellulose content of the feedstock prior to pretreatment.

Another startling feature of biomass that has been pretreated by single-stage autohydrolysis to very low severity levels is that the concentrations of pretreatment by-products that serve as inhibitors of fermentative organisms are kept to very low levels. Consequently, it is often possible to use hydrolysed biomass obtained by methods of the invention directly in fermentations, without requirement for any washing or other detoxification step. As is well known in the art, autohydrolysis hydrothermal pretreatment typically produces a variety of soluble by-products which act as "fermentation inhibitors," in that these inhibit growth and/or metabolism of fermentative organisms. Different fermentation inhibitors are produced in different amounts, depending on the properties of the lignocellulosic feedstock and on the severity of pretreatment. At least three categories of fermentation inhibitors are typically formed during autohydrolysis pretreatment: (1) furans, primarily 2-furfural and 5 hydroxymethylfurfural (5-HMF) which are degradation products from mono- or oligo-saccharides; (2) monomeric phenols, which are degradation products of the lignin structure; and (3) small organic acids, primarily acetic acid, which originate from acetyl groups in hemicellulose and lignin. The mixture of different inhibitors is believed to act synergistically to inhibit microorganisms such as yeasts and *E. coli*.

In some embodiments, pretreated biomass is subjected to flash evaporation using methods well known in the art, in order to reduce levels of volatile inhibitors, most notably furfural. When using autohydrolysis with typical strains of biomass feedstocks, such as wheat straw, sweet sorghum bagasse, sugar cane bagasse, corn stover, and empty fruit bunches, pretreated to xylan number 10% or higher, it is believed that acetic acid and furfural levels are potentially inhibitory to fermentative organisms. Where biomass feedstocks are pretreated at DM 35% or higher to xylan number 10% or higher, and where solid fraction is subsequently hydrolysed enzymatically at 25% or lower DM, with added water to adjust DM but without washing steps, furfural levels in the hydrolysate can typically be kept under 3 g/kg and acetic acid levels beneath 9 g/kg. These levels are typically acceptable for yeast fermentations using specialized strains. During enzymatic hydrolysis, some additional acetic acid may be released from degradation of hemicellulose in the solid fraction. In some embodiments, it may be advantageous to remove some acetic acid content from liquid fraction and/or hydrolysed solid fraction using electrodialysis and/or other methods known in the art.

Lignocellulosic biomass, such as soft lignocellulosic biomass feedstocks, such as agricultural waste such as cereal straw, e.g. wheat, barley, rye or sorghum straw, grass, leaves, sugar cane bagasse, sweet sorghum bagasse, corn stover, and empty fruit bunches etc. are pretreated, usually preceded by a cleaning step, where e.g. sand, stones, foreign objects and the like are removed, and/or after a by single-stage autohydrolysis to xylan number 10% or higher typically comprise a small component of C6 monomers (1x), primarily glucose with some other sugars; a larger component of soluble C6 oligomers (about 2x-7x); a larger component of C5 monomers (about 4x-8x), primarily xylose with some arabinose and other sugars; and a much larger component of soluble xylo-oligomers (about 18x-30x) wherein "nx" refers to the number of sugar units, i.e. 1x=monomer, 2x=dimer, and so forth. Soluble xylo-oligomers typically include primarily xylohexose, xylopentose, xylotetraose, xylotriose and xylobiose with some higher chain oligomers. Xylo-oligomers can also be modified, such as esterified.

Different feedstocks can be pretreated using single-stage autohydrolysis to e.g. xylan number 10% or greater by a variety of different combinations of reactor residence times and temperatures. One skilled in the art will readily determine through routine experimentation an appropriate pretreatment routine to apply with any given feedstock, using any given reactor, and with any given biomass reactor-loading and reactor-unloading system. Where feedstocks are pretreated using a continuous reactor, loaded by either a sluice-system or a screw-plug feeder, and unloaded by either a "particle pump" sluice system or a hydrocyclone system, very low severity of 10% or greater xylan number can e.g. be achieved using typical strains of wheat straw or empty fruit bunches by a temperature of 180° C. and a reactor residence time of 24 minutes. For typical biomass feedstocks, such as soft lignocellulosic biomass from commonly used varieties of corn stover, sugar cane bagasse, and sweet sorghum bagasse, it is believed that low severities, such as xylan numbers >10% can be achieved using a temperature of around 180° C. and a reactor residence time of around 12 minutes, or using a temperature of around 175° C. and a reactor residence time of around 17 minutes. It will be readily understood by one skilled in the art that residence times and temperatures maybe adjusted to achieve comparable levels of $R_0$ severity. Following pretreatment, pretreated biomass is separated into a solid fraction and a liquid fraction by a solid/liquid separation step. It will be readily understood that "solid fraction" and "liquid fraction" may be further subdivided or processed. In some embodiments, biomass may be removed from a pretreatment reactor concurrently with solid/liquid separation. In some embodiments, pretreated biomass is subject to a solid/liquid separation step after it has been unloaded from the reactor, typically using a simple and—low cost screw press system, to generate a solid fraction and a liquid fraction. Cellulase enzyme activities are inhibited by liquid fraction, most notably due to xylo-oligomer content but possibly also due to phenol content and/or other compounds not yet identified. It can be advantageous to achieve the highest practicable levels of dry matter content in the solid fraction or, alternatively, to remove the highest practicable amount of dissolved solids from the solid fraction. In some embodiments, solid/liquid separation achieves a solid fraction having a DM content of at least 40%, at least 45%, at least 50% or at least 55%. Solid/liquid separation using ordinary screw press systems can typically achieve DM levels as high as 50% in the solid fraction, especially when the biomass feedstock has been pretreated and processed in such manner that fiber structure is maintained.

In some embodiments, it may be advantageous to incur higher plant capital expenses in order to achieve more effective solid/liquid separation, for example, using a membrane filter press system. In some embodiments, dissolved solids can be removed from a solid fraction by serial washing and pressing or by displacement washing techniques known in the pulp and paper art. In some embodiments, either by solid/liquid separation directly, or by some combination of washing and solid/liquid separation, the dissolved solids content of the solid fraction is reduced by at least 50%, at least 55%, at least 60%, at least 65%, at least 70% or at least 75%. Enzymatic hydrolysis of feedstocks pretreated to xylan number 10% or higher can typically be conducted with commercially reasonable enzyme consumption, without requirement for specific washing or de-toxification steps, where the solid fraction is pressed to at least 40% DM, or where dissolved solids content of the solid fraction is reduced by at least 50%.

In some embodiments, hydrothermal pretreatment is conducted without supplemental oxygen as required for wet oxidation pretreatments, or without addition of organic solvent as required for organosolv pretreatment, or without use of microwave heating as required for microwave pretreatments. In some embodiments, hydrothermal pretreatment is conducted at temperatures of 140° C. or higher, or at 150° C. or higher, or at 160° C. or higher, or between 16° and 200° C., or between 170 and 190° C., or at 180° C. or lower, or at 170° C. or lower. In some embodiments, some C5 content may be removed by a soaking step prior to pressurized pretreatment. In some embodiments, the single reactor may be configured to heat biomass to a single target temperature. Alternatively, the single reactor may be configured to affect a temperature gradient within the reactor such that biomass is exposed, during a single passage, to more than one temperature region. In some embodiments, it may be advantageous to partially remove some solubilized biomass components from within the pressurized reactor during the course of pretreatment.

Suitable hydrothermal pretreatment reactors typically include most pulping reactors known from the pulp and paper industry. In some embodiments, hydrothermal pretreatment is administered by steam within a reactor pressurized to 10 bar or lower, or to 12 bar or lower, or to 4 bar or higher, or 8 bar or higher, or between 8 and 18 bar, or between 18 and 20 bar. In some embodiments, the pretreatment reactor is configured for a continuous inflow of feedstock.

In some embodiments, wetted biomass is conveyed through the reactor, under pressure, for a certain duration or "residence time." Residence time is advantageously kept brief to facilitate higher biomass throughput. However, the pretreatment severity obtained is determined both by temperature and by residence time. Temperature during hydrothermal pretreatment is advantageously kept lower, not only because methods of the invention seek to obtain a very low pretreatment severity, but also because lower temperatures can be accomplished using lower steam pressures. To the extent that pretreatment temperature can be at levels of 180° C. or lower, and accordingly, saturated steam pressures kept to 10 bar or lower, lower tendency for corrosion is experienced and much lower grade pressure fittings and steel compositions may be used, which reduces plant capital costs. In some embodiments, the reactor is configured to heat biomass to a single target temperature between 16° and 200° C., or between 17° and 190° C.

Residence times in some embodiments are less than 60, less than 30, less than 20, less than 15, less than 14, less than 3, less than 12, less than 10, less than 8, or less than 5 minutes. Further embodiments relating to suitable residence times may be disclosed elsewhere.

Biomass feedstocks, such as lignocellulosic biomass, may be loaded from atmospheric pressure into a pressurized reactor by a variety of means. In some embodiments, a sluice-type "particle pump" system may be used to load biomass feedstocks, such as the systems described in e.g. WO 2003/013714 or WO 2011/024145, both of which being hereby incorporated by reference in entirety. In some embodiments, it may be advantageous to load a pretreatment reactor using a so-called "screw plug" feeder.

Pretreated biomass may be unloaded from a pressurized reactor by a variety of means. In some embodiments, pretreated biomass is unloaded in such manner as to preserve the fiber structure of the material. Preserving the fiber structure of the pretreated biomass is advantageous because this permits the solid fraction of the pretreated material to be pressed during solid/liquid separation to comparatively high dry matter levels using ordinary screw press equipment, and thereby avoiding the added expense and complexity of membrane filter press systems. Fiber structure can be maintained by removing the feedstock from the pressurized reactor in a manner that is non-explosive. In some embodiments, non-explosive removal may be accomplished and fiber structure thereby maintained using sluice-type systems, such as those described earlier. In some embodiments, non-explosive removal may be accomplished and fiber structure thereby maintained using a hydrocyclone removal system, such as those described in WO 2009/147512, which are hereby incorporated by reference in entirety.

In some embodiments, pretreated biomass can be removed from a pressurized pretreatment reactor using "steam explosion," which involves explosive release of the pretreated material. Steam-exploded, pretreated biomass does not retain its fiber structure and accordingly requires more elaborate solid/liquid separation systems in order to achieve dry matter content comparable to dry matter contents, which can be achieved using e.g. conventional screw press systems with pretreated biomass that retains its fiber structure.

As will be readily understood by one skilled in the art, the composition of enzyme mixtures suitable for practicing methods of the invention may vary within comparatively wide bounds. Suitable enzyme preparations include commercially available xylanase preparations and cellulase preparations optimized for lignocellulosic biomass conversion. Selection and modification of enzyme mixtures during optimization may include genetic engineering techniques. Commercially available cellulase preparations optimized for lignocellulosic biomass conversion are typically identified by the manufacturer and/or purveyor as such. These are typically distinct from commercially available cellulase preparations for general use or optimized for use in production of animal feed, food, textiles detergents or in the paper industry. In some embodiments, a commercially available cellulase preparation optimized for lignocellulosic biomass conversion is used, such as one that is e.g. provided by GENENCOR™ (now DuPont), DSM or NOVOZYMES™. Usually, such compositions comprise cellulase(s) and/or hemicellulase(s), such as one or more of exoglucanases, endoglucanases, endoxylanases, xylosidases, acetyl xylan esterases and beta glucosidases, including any combination thereof. Such enzymes can e.g. be isolated from fermentations of genetically modified *Trichoderma reesei*, such as, for example, the commercial cellulase preparation sold under the trademark ACCELLERASE TRIO™.

In some embodiments, a commercially available cellulase preparation optimized for lignocellulosic biomass conversion is used that is provided by NOVOZYMES™ and that comprises exoglucanases, endoglucanases, endoxylanases, xylosidases, acetyl xylan esterases and beta glucosidases, such as, for example, the commercial cellulase preparations sold under either of the trademarks Cellic® CTec2 or Cellic® CTec3.

It is believed that the specific enzyme activities present in different commercially available cellulase preparation optimized for lignocellulosic biomass conversion can be analysed in detail using methods known in the art.

Three different cellulase preparations, Accellerase® TRIO™ from DuPont (and/or GENENCOR) and Cellic® CTec2 and Cellic® CTec3 from NOVOZYMES™, are believed to be effective at enzyme dose levels within the manufacturers' suggested range.

Suitable cellulase preparations optimized for lignocellulosic biomass conversion usually comprise multiple enzyme activities, including exoglucanase, endoglucanase, hemicellulases (including xylanases) and β-glucosidases. Enzyme preparations can be expressed in different activities/units, such as carboxymethycellulase (CMC U) units, acid birchwood xylanase units (ABXU), and pNP-glucosidase units (pNPG U). For example, ACCELLERASE TRIO™ comprises: endoglucanase activity: 2000-2600 CMC U/g, xylanase activity: >3000 ABX U/g, and beta-glucosidase activity: >2000 pNPG U/g; wherein one CMC unit of activity liberates 1 μmol of reducing sugars (expressed as glucose equivalents) in one minute at 50° C. and pH 4.8; one ABX unit is defined as the amount of enzyme required to generate 1 μmol of xylose reducing sugar equivalents per minute at 50° C.; and pH 5.3; and one pNPG unit denotes 1 μmol of nitro-phenol liberated from para-nitrophenyl-B-D-glucopyranoside per minute at 50° C. and pH 4.8.

Based on the available information in the public domain, it is believed that a person skilled in the art is able to provide enzyme preparations suitable for enzymatic hydrolyses according to the present invention, in particular for any one of the enzymatic hydrolysis steps disclosed herein, such as fiber hydrolysis, fiber cake hydrolysis and MSH (mixed sugar hydrolysis).

The current invention appears well suited for industrial applications, including large-scale industrial applications. In some embodiments, methods of the invention are practiced using at least about 100, 200, 500 kg biomass feedstock, or at least 1000 kg, or at least 5000 kg.

In a first aspect, the current invention pertains to a method for providing a C5/C6 product from a lignocellulosic material comprising the steps:
  a) Pretreatment of the lignocellulosic material;
  b) Solid/liquid separation of the pretreated lignocellulosic material from step (a) into a first solid fraction and a first liquid fraction;
  c) Enzymatic fiber hydrolysis of said first solid fraction from step (b) by use of an enzyme composition capable of degrading lignocellulosic material, thereby providing a C5/C6 fiber slurry comprising C5 and/or C6 sugars;
  d) Solid/liquid separation of the C5/C6 fiber slurry from step (c) into a second solid fraction and a second liquid fraction; and optionally
  e) Combining said first liquid fraction and said second liquid fraction for enzymatic mixed sugar hydrolysis (MSH), whereby a MSH C5/C6 product is provided.

In some embodiments, said method may also comprise a further step (f): Enzymatic fiber cake hydrolysis of said second solid fraction from step (d) to obtain a slurry C5/C6 product.

According to the present invention, suitable lignocellulosic biomass may comprise soft lignocellulosic biomass such as wheat straw, corn stover, corn cobs, empty fruit bunches, rice straw, oat straw, barley straw, canola straw, rye straw, sorghum, sweet sorghum, soybean stover, switch grass, Bermuda grass and other grasses, bagasse, beet pulp, corn fiber, or any combinations thereof. Lignocellulosic biomass may comprise other lignocellulosic materials such as wood, wood chips, but also paper, newsprint, cardboard, or other municipal or office wastes. Lignocellulosic biomass may be used as a mixture of materials originating from different feedstocks, it may be fresh, partially dried, fully dried or any combination thereof. Commonly, the lignocellulosic biomass is considered a waste product.

In some embodiments, the lignocellulosic material is soft lignocellulosic biomass, e.g. agricultural waste such as one or more of wheat straw, corn stover, corn cobs, empty fruit bunches, rice straw, oat straw, barley straw, canola straw, rye straw, sorghum, sweet sorghum, soybean stover, switch grass, Bermuda grass and other grasses, bagasse, beet pulp, corn fiber, or any combinations thereof. In some embodiments, the lignocellulosic biomass may also be predominantly or entirely ensiled biomass, or comprise ensiled biomass, such as at least 5, 10, 25, 50%, 75%, 90%, 95%, 99% or more ensiled biomass.

in some embodiments, the lignocellulosic material is not soft lignocellulosic biomass. Examples of such non-soft lignocellulosic biomass comprise e.g. wood, wood chips, bark, branches, but also paper, newsprint, cardboard, or even municipal waste, such as sorted or unsorted municipal waste, or office wastes. In some embodiments, the lignocellulosic biomass may also be predominantly or entirely non-soft lignocellulosic biomass, or comprise non-soft lignocellulosic biomass, such as at least 5, 10, 25, 50% or more than 50% non-soft lignocellulosic biomass.

In some embodiments, the pretreatment is conducted at a dry matter (DM) content in the range of 5-80%, such as 10-70%, such as 20-60%, or such as 30-50%, or at a DM content around 5%, 10%, 15%, 20%, 25%, 30%, 35%, 40%, 45%, 50%, 55%, 60%, 65%, 70%, 75%, 80% or at a DM content of more than 80%. In some other embodiments, the pretreatment is conducted at a DM content of 5-10%, 10-20%, 20-30%, 30-40%, 40-50%, 50-60%, 60-70%, or even 70-80%. In some further embodiments, the pretreatment is conducted at a DM content of or around 5%, 10%, 15%, 20%, 25%, 30%, 35%, 40%, 45%, 50%, 55%, 60%, 65%, 70%, 75%, 80% or at a DM content of more than 80%.

In some embodiments, pretreatment is conducted at low, medium, or high severity. In some embodiments, pretreatment is conducted at conditions providing a xylan number of >10%, 6-10% or <6%. It is believed that relevant advantages according to the invention can also be obtained at medium, or high pretreatment severities. In some embodiments, the biomass feedstock is pretreated at medium severity, such that the pretreated biomass is characterized by having a xylan number of 6-10%. In some embodiments, the biomass is pretreated to a xylan number of 6-7%, 7-8%, or 9-10%. In further embodiments, the biomass feedstock is pretreated at high severity, such that the pretreated biomass is characterized by having a xylan number of less than 6%. In some embodiments, the biomass is pretreated to a xylan number of below 6%, 5% or lower, 4% or lower, 3% or lower, 2% or lower, or 1% or lower.

In some embodiments, enzymatic fiber hydrolysis, fiber cake hydrolysis and/or MSH is/are conducted for a period of at least 6 h, 12 h, 24 h, 48 h, or 72 h, such as 6-120 h, 12-100 h, or 48-96 h, or around 12 h, 24 h, 48 h, 72 h, 96 h, or 120 h.

In some embodiments, enzymatic fiber hydrolysis, fiber cake hydrolysis and/or MSH is/are conducted at a pH in the range of at least pH 3.0, such as in the range of pH 3.0-6.0, such as pH 4.0-5.5, and/or such as pH 4.2-5.4.

In some embodiments, enzymatic fiber hydrolysis, fiber cake hydrolysis and/or MSH is/are conducted at a pH of around 4.2, 4.5, 4.7, 4.8, 4.9, 5.0, 5.1, 5.2, 5.3 or 5.4.

In some embodiments, enzymatic fiber hydrolysis, fiber cake hydrolysis and/or MSH is/are conducted at a temperature in the range of 30-70° C., 40-65° C., 50-62° C., or 55-60° C., and/or around 40° C., 42° C., 44° C., 46° C., 48° C., 50° C., 52° C., 54° C., 56° C., 58° C., 60° C., 62° C., 64° C., 66° C., 68° C., or 70° C.

In some embodiments, enzymatic fiber hydrolysis, fiber cake hydrolysis and/or MSH is/are conducted at a suitable DM content, such as a DM content of at least 10%, such as 15%. In some embodiments, the DM content is around 15-45%, 20-40%, 25-35%, and/or at a DM content around 15%, 20%, 25%, 30%, 35%, or 40%. In some embodiments, the DM content is around 40% or higher.

In some embodiments, the enzyme composition capable of degrading lignocellulosic material comprises a cellulase and/or a hemicellulase.

In some embodiments, the enzyme composition capable of degrading lignocellulosic material comprises a mixture of cellulase(s) and/or hemicellulase(s).

In some embodiments, the hemicellulase is or comprises one or more xylanase(s), xylosidase(s), arabinoxylanase(s), xyloglucanase(s), glucoronoxylanase(s), glucomannanase(s), esterase(s), and any combination thereof.

Sugars, such as C5 and/or C6 mono-, oligo- and/or polymers can be modified, such as esterified, e.g. comprising ferulic acid. Ferulic acid can be efficiently released by esterase(s), such as a ferulic acid esterase, e.g. FAE-III from *Aspergillus niger* (see Faulds and Williamson, Appl. Microbiol. Biotechnol. 1995 November; 43(6): 1082-7), which released ferulic acid from wheat bran. Said release was improved in the presence of a xylanase, such as a *Trichoderma viride* xylanase. Hence, in some embodiments an esterase, such as a ferulic acid esterase, and optionally cellulase and/or at least one xylanase are added in an enzymatic hydrolysis step, such as any one of fiber hydrolysis, fiber cake hydrolysis, and/or mixed sugar hydrolysis.

In some embodiments, the esterases comprise one or more acetylesterases and/or feroyl esterases.

In some embodiments, the enzyme composition capable of degrading lignocellulosic material comprises one or more of endocellulase(s), endoglucanase(s), exocellulase(s), exoglucanase(s), endoxylanase(s), acetyl xylan esterase(s), xylosidase(s), β-glucosidase and any combination thereof.

In some embodiments, said method for providing a C5/C6 product from a lignocellulosic material comprises step (e), i.e. combining said first liquid fraction and said second liquid fraction for enzymatic mixed sugar hydrolysis (MSH). Through combining said first liquid fraction and said second liquid fraction and enzymatically hydrolysing the mixture, a MSH C5/C6 product is provided.

In some embodiments, hemicellulase(s) are also present in step (e).

In some embodiments, the hemicellulase(s) present in step (e) comprises xylanase(s), xylosidase(s), arabinoxylanase(s), xyloglucanase(s), glucoronoxylanase(s), glucomannanase(s), esterase(s), acetylesterases, feroyl esterase(s), and any combination thereof.

In some embodiments, all or at least a fraction of the hemicellulase(s) present in step (e) has been added in step (c).

In some embodiments, one or more hemicellulase(s) is/are added in step (e).

In some embodiments, wherein one or more additional enzyme(s) are added in step (e). In some further embodiments, the additional enzyme(s) is essentially not present (e.g. less than 1% of total enzyme activity, present as only a minor side activity and/or contamination etc.) in the enzyme composition capable of degrading lignocellulosic material added in step (c). In other embodiments, the additional enzyme(s) is one or more of: hemicellulase(s), xylanase(s), xylosidase(s), arabinoxylanase(s), xyloglucanase(s), glucoronoxylanase(s), glucomannanase(s), esterase(s), acetylesterases, feroyl esterase(s), and any combination thereof.

In some embodiments step e) comprises an ultrafiltration step for separation of the hydrolysed sugars present in the permeate from the hemicellulase(s) present in the retentate such as to recycle at least part of the hemicellulase(s). Cost of enzymes constitute a significant proportion of the variable costs of the method, and the ultrafiltration step limits this cost by recycling of the hemicellulase(s). Thus, in some embodiments, said step (e) comprises or is followed by an ultrafiltration step (j) for recycling enzymes present after MSH. In further embodiments, the ultrafiltration step (j) is adapted to allow for recycling of at least 30% (w/w), 50% (w/w), 75% (w/w), 80% (w/w), or 90% (w/w) of the enzyme activity.

In some embodiments, cellulase(s) is/are also present in step (f). In some embodiments, at least one cellulase has been added such that said second solid fraction in step (f) comprises at least one cellulase. In some embodiments, the cellulose(s) present in step (f) has been added in step (c). Cellulases bind to the fibers in the solid fraction and thus adding cellulase to the solid fraction from step (b) may serve to complete the hydrolysis performed in both step (c) (fiber hydrolysis) and step (f) (fiber cake hydrolysis). Hence, in some embodiments, all, or essentially all of the cellulase present in step (f) has been added in step (c).

In some embodiments, at least a fraction of the cellulase used in step (f) has been added in step (c).

In some embodiments, one or more cellulase(s) and optionally hemicellulase(s) is/are added in step (f).

In some embodiments, cellulase(s) and/or hemicellulase(s) are added in step (c), such as by the addition of a mixture comprising one or more cellulase and one or more hemicellulase.

In some embodiments, the MSH and/or fiber cake hydrolysis are performed without addition of one or more enzyme(s).

In some embodiments, the MSH and/or fiber cake hydrolysis are performed without addition of one or more cellulose(s) and/or one or more hemicellulose(s).

In some embodiments, said method for providing a C5/C6 product from a lignocellulosic material comprises step (g), namely solid/liquid separation of the slurry C5/C6 product from step (f) into a third solid fraction and a liquid C5/C6 product.

In some embodiments, the second liquid fraction possesses a lower inhibitor concentration than the first liquid fraction.

In some embodiments, the second liquid fraction possesses a lower inhibitor concentration than the MSH C5/C6 product.

In some embodiments, the slurry C5/C6 product" possesses a lower inhibitor concentration than the MSH C5/C6 product.

In some embodiments, said method for providing a C5/C6 product from a lignocellulosic material comprises step (k), i.e. combining at least a portion of the MSH C5/C6 product with at least a portion of one or more of: the slurry C5/C6 product from step (f), the liquid C5/C6 product from step (g), and/or the second liquid fraction from step (d) to obtain a combined C5/C6 product. In some embodiments, the combined C5/C6 product consists or consists essentially of the MSH C5/C6 product and the slurry C5/C6 product from step (f); the MSH C5/C6 product and the liquid C5/C6 product from step (g); or the MSH C5/C6 product and the second liquid fraction from step (d).

In some embodiments, the combined C5/C6 product possesses a ratio of MSH C5/C6 product to liquid C5/C6 product; slurry C5/C6 product or second liquid fraction from step (d) in the range of 100:0.1-0.1:100 (w/w), such as 10:0.1-0.1:10 (w/w), or such as 10:1-1:10 (w/w), such as 5:1-1:5 (w/w); such as 4:1-1:4 (w/w), such as 3:1-1:3 (w/w), such as 2.5-1:2.5 (w/w), such as 2:1-1:2 (w/w) or such as 1.5-1:1-1.5 (w/w).

In some embodiments, the combined C5/C6 product possesses a ratio of MSH C5/C6 product to liquid C5/C6 product; slurry C5/C6 product or second liquid fraction from step (d) is in the range 50:1 (w/w), 25:1 (w/w), 20:1 (w/w), 15:1 (w/w), 10:1 (w/w), 9:1 (w/w), 8:1 (w/w), 7:1 (w/w), 6:1 (w/w), 5:1 (w/w), 4:1 (w/w), 3:1 (w/w), 2:1 (w/w), 1:1 (w/w), 1:1.5 (w/w), 1:2 (w/w), 1:2.5 (w/w), 1:3 (w/w), 1:4 (w/w), 1:5 (w/w), 1:6 (w/w), 1:7 (w/w), 1:8 (w/w), 1:9 (w/w), 1:10 (w/w), 1:15 (w/w), 1:20 (w/w), 1:25 (w/w), or 1:50 (w/w). In some preferred embodiments, said ratio is, or is about 1:1.5 (w/w), 1:2 (w/w), or 1:2.5 (w/w).

In some embodiments, said method for providing a C5/C6 product from a lignocellulosic material comprises a lignin recovery step. This step may comprise on or more of: removal of water, compacting and/or pelleting.

In some embodiments, said lignin recovery is conducted on the second or third solid fraction provided in steps (d) or (g).

In some embodiments, any C5/C6 product is a C5+C6 product, i.e. a product comprising C5 and C6 carbohydrates, such as xylose and glucose, including structural analogues, isomers and/or derivatives thereof.

In some embodiments, the C5+C6 product comprises glucose and xylose.

In a second aspect, the current invention relates to a method for providing a fermentation product, said method comprising the steps of:
  m) Providing at least one C5/C6 product according to the method of any one of the preceding embodiments according to the first aspect; and
  n) Providing the fermentation product by a fermentation of said C5/C6 product with a microorganism.

In some embodiments, the C5/C6 product comprises one or more of: MSH C5/C6 product, Slurry C5/C6 product, Liquid C5/C6 product, Combined C5/C6 product, first liquid fraction, or second liquid fraction, and any combination thereof.

Usually, the fermentation product is provided in a fermentation broth. Thus, in some embodiments said method of providing a fermentation product comprising a further step (o): recovering said fermentation product from a fermentation broth.

In some embodiments, said method comprises step (p): recovering lignin from a spent fermentation broth, and/or a fraction provided in steps (n) or (o).

In some embodiments, the fermentation is carried out in at least a first and a second fermentation step, wherein a first and a second fermentation substrate are fermented.

Providing two fermentation substrates with different inhibitor and/or fermentation inhibitor concentration can be advantageous, in particularly useful when the fermentation is carried out by a microorganism sensitive to said inhibitors, which are predominantly present in the C6+C5 product obtained in step b). An increased productivity of the fermentation can thereby be achieved, e.g. through a shorter duration of the fermentation, and or higher product yield.

In particular, when also the combined fractions of the MSH C5/C6 product+slurry or liquid C5/C6 product comprise too high inhibitor concentration, the current invention provides an alternative that does not require diluting the fermentation substrate with water, which is not desirable. Such dilution with water could be performed in a first fermentation, such as a batch fermentation, before fermenting the combined fractions in e.g. a fed-batch fermentation.

In some embodiments, the present invention relates to a method as defined in the previous embodiments wherein said fermentation is carried out by first batch-fermenting the liquid C5/C6 product obtained e.g. in step (g) or the slurry C5/C6 product obtained in step (f) and subsequently by fed-batch-fermenting the MSH C5/C6 product obtained in step (e) or (j), usually in combination with further quantities of liquid C5/C6 product obtained e.g. in step (g) or the slurry C5/C6 product obtained in step (f).

Further embodiments related to two-step fermentations are also presented below.

In a third aspect, the current invention concerns a two-step fermentation method comprising the steps of:
aa) Pretreatment of the lignocellulosic material;
bb) Solid/liquid separation of the pretreated lignocellulosic material from step (aa) into a first solid fraction and a first liquid fraction;
cc) Enzymatic fiber hydrolysis of said first solid fraction from step (bb) by use of an enzyme composition capable of degrading lignocellulosic material, thereby providing a C5/C6 fiber slurry;
dd) Solid/liquid separation of the C5/C6 fiber slurry from step (cc) into a second solid fraction and a second liquid fraction;
ee) Enzymatic mixed sugar hydrolysis (MSH) of a mixture of the first liquid fraction from step (bb) and the C5/C6 fiber slurry from step (cc), or the first liquid fraction from step (bb) and the second liquid fraction from step (dd), thereby providing a C5/C6 MSH product;
ff) Providing a first fermentation substrate comprising at least a portion of the C5/C6 fiber slurry and/or the second liquid fraction;
gg) Providing a second fermentation substrate comprising at least a portion of the C5/C6 MSH product;
hh) Fermenting the first fermentation substrate in a first fermentation with a microorganism; and
ii) Fermenting the second fermentation substrate in a subsequent second fermentation;
wherein step (dd) is optional.

In some embodiments, either one of steps aa, bb, cc, dd and/or ee may correspond to steps a, b, c, d and/or e according to any one of the previous aspects, respectively.

In some embodiments, the first fermentation substrate possesses a significantly lower inhibitor concentration than the second fermentation substrate.

In some embodiments, the first fermentation is a batch or fed-batch fermentation.

In some embodiments, the first fermentation is carried out by providing a first fermentation substrate comprising: (i) the second liquid fraction provided in step (d) or (dd); (ii) the C5/C6 fiber slurry provided in step (c) or (cc); and/or (iii) the C5/C6 product obtained in step (f), i.e. the liquid C5/C6 product or the slurry C5/C6 product.

In some embodiments, the first fermentation is carried out by providing a first fermentation substrate consisting essentially of: (i) the second liquid fraction provided in step (d) or (dd); (ii) the C5/C6 fiber slurry provided in step (c) or (cc); and/or (iii) the C5/C6 product obtained in step (f), i.e. the liquid C5/C6 product or the slurry C5/C6 product.

In some embodiments, the first fermentation substrate comprises or consists essentially of a mixture of the second liquid fraction and the C5/C6 product obtained in step (f), i.e. the liquid C5/C6 product or the slurry C5/C6 product.

In some embodiments, the ratio between the second liquid fraction and the C5/C6 product is in the range of 100:0.1-0.1:100 (w/w), such as 10:0.1-0.1:10 (w/w), or such as 10:1-1:10 (w/w).

In some embodiments, the ratio of the second liquid fraction and the C5/C6 product is in the range of or around 50:1 (w/w), 25:1 (w/w), 20:1 (w/w), 15:1 (w/w), 10:1 (w/w), 9:1 (w/w), 8:1 (w/w), 7:1 (w/w), 6:1 (w/w), 5:1 (w/w), 4:1 (w/w), 3:1 (w/w), 2:1 (w/w), 1:1 (w/w), 1:2 (w/w), 1:3 (w/w), 1:4 (w/w), 1:5 (w/w), 1:6 (w/w), 1:7 (w/w), 1:8 (w/w), 1:9 (w/w), 1:10 (w/w), 1:15 (w/w), 1:20 (w/w), 1:25 (w/w), or 1:50 (w/w).

In some embodiments, the first fermentation substrate is provided essentially without dilution with process water.

In some embodiments, the second fermentation is a fed-batch fermentation or a continuous fermentation, optionally conducted in the same fermenter as the first fermentation.

In some embodiments, said fed-batch fermentation is conducted using linear or exponential feed.

In some embodiments, wherein the second fermentation is conducted with the same microorganisms as in the first fermentation.

In some embodiments, the second fermentation is carried out by providing a second fermentation substrate comprising or consisting essentially of a mixture of the C5/C6 product obtained in step (f) (i.e. the liquid C5/C6 product or slurry C5/C6 product) and the C5/C6 product obtained from step (e) (i.e. MSH C5/C6 product).

In some embodiments, the ratio between the liquid C5/C6 product or slurry C5/C6 product and the C5/C6 product obtained from step (e) (i.e. MSH C5/C6 product) is in the range of 100:0.1-0.1:100 (w/w), such as 10:0.1-0.1:10 (w/w), or such as 10:1-1:10 (w/w), such as 5:1-1:5 (w/w); such as 4:1-1:4 (w/w), such as 3:1-1:3 (w/w), such as 2.5-1:2.5 (w/w), such as 2:1-1:2 (w/w) or such as 1.5-1:1-1.5 (w/w). In some preferred embodiments, said ratio is 2.5-1:2.5 (w/w).

In some embodiments, the ratio between the liquid C5/C6 product or slurry C5/C6 product and the C5/C6 product obtained from step (e) (i.e. MSH C5/C6 product) is in the range of or around 50:1 (w/w), 25:1 (w/w), 20:1 (w/w), 15:1 (w/w), 10:1 (w/w), 9:1 (w/w), 8:1 (w/w), 7:1 (w/w), 6:1 (w/w), 5:1 (w/w), 4:1 (w/w), 3:1 (w/w), 2:1 (w/w), 1:1 (w/w), 1:1.5 (w/w), 1:2 (w/w), 1:2.5 (w/w), 1:3 (w/w), 1:4 (w/w), 1:5 (w/w), 1:6 (w/w), 1:7 (w/w), 1:8 (w/w), 1:9 (w/w), 1:10 (w/w), 1:15 (w/w), 1:20 (w/w), 1:25 (w/w), or 1:50 (w/w). In some preferred embodiments, said ratio is, or is about 1:1.5 (w/w), 1:2 (w/w), or 1:2.5 (w/w).

In some embodiments, the second fermentation is carried out by providing a second fermentation substrate comprising or consisting essentially of the C5/C6 MSH product provided in step (ee).

In some embodiments, the second fermentation is provided essentially without dilution with of process water.

In some embodiments, the volume of the first fermentation is significantly smaller than the volume of the second fermentation.

In some embodiments, the volume of the first fermentation is 2-40%, 3-30%, 5-20%, 7.5-15%, 8-12%, or around 10% of the volume of the second fermentation.

In some embodiments, the volume of the first fermentation is around 5, 7.5, 10, 15, 20, 25, 30, 35 or 40% of the volume of the second fermentation.

In some embodiments, the fermentation product is recovered by distillation.

In some embodiments, said fermentation method comprises a lignin recovery step, such as a lignin recovery step from a distillation remnant.

In some embodiments, the first and second fermentation are consecutive fermentations, optionally conducted in the same fermenter.

In some embodiments, the second fermentation comprises fermentation of both the first liquid fraction and the C5/C6 fiber slurry.

In some embodiments, the fermentation product is an alcohol, organic acid, vitamin, amino acid, peptide, enzyme or the like.

In some embodiments, the fermentation product is a C1-C4 product.

In some embodiments, the C1-C4 product is one or more of: methanol, ethanol, butanol, acetone, formic acid, acetic acid, propionic acid, butyric acid, oxalic acid, lactic acid, malic aid, and/or any combination thereof.

In some embodiments, the C1-C4 product is EtOH.

In some embodiments, the microorganism is a eukaryotic or prokaryotic microorganism, such as a bacterium or a yeast.

In some embodiments, the microorganism is a recombinant microorganism.

In some embodiments, the microorganism is capable of fermenting C5 and C6 sugars, such as xylose and glucose.

A variety of microorganisms may be used for the fermentation of the C6+C5 product(s) into one or more fermentation product(s), such as C1-C4 product such as ethanol, acetone and/or organic acid(s), such as lactic or acetic acid, optionally also alone or in combination with larger organic acids, such as valeric acid, caproic acid, citric acid, or benzoic acid. As will be readily understood by one skilled in the art, various yeast strains are available which are suitable for converting C6 sugars as well as C5 sugars into ethanol, e.g. various *Saccharomyces cerevisiae* strains. Also, for fermentations to produce lactic acid a range of suitable microorganisms are available, such as lactic acid bacteria, such as *Lactococcus* spp., *Lactobacillus* spp, etc. In some embodiments, the microorganism is a *Lactococcus* spp., *Lactobacillus* spp.

In some embodiments, the microorganism is a yeast, such as a *Saccharomyces cerevisiae* capable of or adapted to fermenting xylose and glucose to EtOH.

In some embodiments, said fermentation is conducted by the use of a microorganism, such as a recombinant microorganism capable of converting C6 sugars and C5 sugars into ethanol.

In some embodiments, said fermentation is conducted by the use of a recombinant microorganism capable of converting glucose and xylose into ethanol.

In some embodiments, the fermentation is conducted with a microorganism that is able to ferment at least one C5 sugar, apart from one or more C6 sugar(s).

In some embodiment, the process is a process for the production of ethanol, whereby the process comprises fermenting a medium containing sugar(s) with a microorganism that is able to ferment at least one C5 sugar, apart from one or more C6 sugar(s).

In some embodiments, the microorganism is able to ferment glucose, L-arabinose and xylose to ethanol.

In some embodiments, the microorganism that is able to ferment at least one C5 sugar, apart from one or more C6 sugar(s) is a yeast. In an embodiment, the yeast belongs to the genus *Saccharomyces*, preferably of the species *Saccharomyces cerevisiae*. EP 1 499 708 describes a process for making *S. cerevisiae* strains able to produce ethanol from L-arabinose.

WO2003/062430 and WO2006/009434 disclose yeast strains able to convert xylose into ethanol. These yeast strains are able to isomerise xylose into xylulose. In some embodiments, the microorganism is a eukaryotic microorganism as disclosed in EP 1 499 708, WO2003/062430, WO2006/009434, or WO2008/041840.

In some embodiments, the microorganism is a genetically modified yeast (e.g. *Saccharomyces cerevisiae*), capable of using L-arabinose and/or to convert L-arabinose into L-ribulose, and/or xylulose 5-phosphate and/or into a desired fermentation product. Said microorganism may comprise the following genetic modifications: (a) a cluster consisting of PPP-genes TAL1, TKL1, RPE1 and RKI1, under control of strong promoters, (b) a cluster consisting of a xyM-gene and the XKSi-gene both under control of constitutive promoters, (c) a cluster consisting of the genes araA, araB and araD and/or a cluster of xylA-gene and the XKSi-gene; and/or (d) deletion of an aldose reductase gene.

In an embodiment, the fermentation process is anaerobic. In another embodiment, the fermentation process is aerobic, optionally under oxygen-limited conditions.

In an embodiment, the fermentation process is under oxygen-limited conditions, such as a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

Preferably, in a process under oxygen-limited conditions, the rate of oxygen consumption is at least 5.5, more preferably at least 6 and even more preferably at least 7 mmol/L/h.

In a fourth aspect, the current invention concerns a method for preparing ethanol and optionally lignin from a lignocellulosic material comprising the steps of:
  Providing at least one C5/C6 product according to a method according to any one embodiment of the preceding aspects;
  Fermentation of said at least one C5/C6 product to convert sugars to ethanol in the fermentation broth with a yeast;
  Isolation of an ethanol rich fraction from the fermentation broth; and optionally
  Isolation of lignin.

In some embodiments, the fermentation is conducted according to a method according any one embodiments relating to the second or third aspect.

In some embodiments, lignin is isolated from the spent fermentation broth or from the remnants from the spent fermentation broth after isolating the ethanol rich fraction.

In a fifth aspect, the current invention pertains to lignin provided from lignocellulosic biomass, such as ligning obtained or obtainable according to any one of the preceding aspects. It is believed that lignin provided according to the current invention, in particular provided by a "V2.x" process is different from lignin known in the art, such as lignin provided according to the a "whole slurry" or V2 process. The lignin obtained is a high-value product provided that the pre-treatment is not based on addition of acids but e.g. conducted in the absence of added acids as described above.

In a sixth aspect, the current invention relates to a C5/C6 product provided according to any one of the preceding aspects.

In a seventh aspect, the current invention concerns a fermentation substrate comprising a C5/C6 product provided by a method according to any one of the preceding aspects.

In an eighth aspect, the current invention pertains to a first or second fermentation substrate provided by a method according to any one of the preceding aspects.

In a ninth aspect, the current invention relates to compositions comprising lignin obtained or obtainable by a method according to any of the previous aspects, including different uses of said lignin-comprising compositions.

In some embodiments, the present invention relates to lignin obtained from the method according to any of the previous aspects, such as a solid fraction from a spent fermentation broth or from the distillation remnants from a distillation of a spent fermentation broth.

In some embodiments, a composition is provided comprising 0.1-99.9, or 1-90% (w/w) lignin.

It is believed that said lignin can be used in bitumen compositions, including asphalt compositions, such as bitumen compositions disclosed in WO2017/088892, said document herewith being incorporated in its entirety.

In some embodiments, a bitumen composition is provided comprising:
a. 1-99.89% (w/w) bitumen;
b. 0.1-50% (w/w) lignin;
c. 0.01-20% (w/w) plasticity modifying agent(s); and
d. 0-95% (w/w) further component(s).

In some embodiments, said plasticity modifying agent is one or more plastomer, one or more thermoplastic elastomer, one or more rubber, one or more viscosity modifier, and/or one or more reactive polymer, including any combination thereof.

In some embodiments, said further component(s) is one or more dispersing agent(s), surfactant(s), hydrotropic agent(s), emulsifier(s), preserving agent(s), anti-foaming agent(s), viscosity modifier(s), reactive polymer(s) and any combination thereof; and/or one or more aggregate(s) and/or filler(s), such natural, manufactured, recycled aggregates, including any combination thereof.

Said lignin-comprising compositions can be used in a wide variety of applications. In some embodiments, said lignin-comprising compositions can be used e.g. in sealing work, road work, paving work, providing a surface layer, providing a sealing layer, providing a road and providing a pavement, providing a top layer of a road.

In some embodiments, said lignin-comprising compositions can be used e.g. in applications relating to (i) agriculture, (ii) buildings and industrial paving, (iii) hydraulics and erosion control, (iv) industrial, (v) paving, (vi) railways, and (vii) recreation, such as ad (i) disinfectants, fence post coating, mulches, mulching paper, paved barn floors, barnyards, feed platforms, protecting tanks, vats, protection for concrete structures, tree paints (protective); ad (ii): water and moisture barriers (above and below ground), floor compositions, tiles, coverings, insulating fabrics, papers, step treads, building papers, caulking compounds, cement waterproofing compounds, glass wool compositions, insulating fabrics, felts, papers, joint filler compounds, laminated roofing shingles, liquid roof coatings, plastic cements, shingles, acoustical blocks, compositions, felts, bricks, damp-proofing coatings, compositions, insulating board, fabrics, felts, paper, masonry coatings, plasterboards, putty, soundproofing, stucco base, wallboard, air-drying paints, varnishes, artificial timber, ebonised timber, insulating paints, plumbing, pipes, treated awnings, canal linings, sealants; ad (iii): catchment areas, basins, dam groutings, dam linings, protection, dyke protection, ditch linings, drainage gutters, structures, embankment protection, groynes, jetties, levee protection, mattresses for levee and bank protection, membrane linings, waterproofing, reservoir linings, revetments, sand dune stabilisation, sewage lagoons, oxidation ponds, swimming pools, waste ponds, water barriers, backed felts, ad (iv): conduit insulation, lamination, insulating boards, paint compositions, papers, pipe wrapping, insulating felts, panel boards, underseal, battery boxes, carbons, electrical insulating compounds, papers, tapes, wire coatings, junction box compound, moulded conduits, black grease, buffing compounds, cable splicing compound, embalming, etching compositions, extenders, explosives, lap cement, plasticisers, preservatives, printing inks, well drilling fluid, armoured bituminised fabrics, burlap impregnation, mildew prevention, sawdust, cork, asphalt composition, acid-proof enamels, mastics, varnishes, acid-resistant coatings, air-drying paints, varnishes, anti-corrosive and anti-fouling paints, anti-oxidants and solvents, base for solvent compositions, baking and heat-resistant enamels, boat deck sealing compound, lacquers, japans, marine enamels, blasting fuses, briquette binders, burial vaults, casting moulds, clay articles, clay pigeons, expansion joints, flowerpots, foundry cores, friction tape, gaskets, mirror backing, rubber, moulded compositions, shoe fillers, soles; ad (v): airport runways, taxiways, aprons, asphalt blocks, brick fillers, bridge deck, surfacing, crack fillers, floors for buildings, warehouses, garages, highways, roads, streets, shoulders, kerbs, gutters, drainage ditches, parking lots, driveways, Portland cement concrete underseal, roof-deck parking, pavements, footpaths, soil stabilisation; ad (vi) ballast treatment, dust laying, paved ballast, sub-ballast, paved crossings, freight yards, station platforms; and ad (vii) dance pavilions, drive-in movies, gymnasiums, sport arenas, playgrounds, school yards, race tracks, running tracks, skating rinks, swimming and wading pools, tennis courts, handball courts, synthetic playing fields and running track surfaces.

Comparison of "Whole Slurry" and "C5 Bypass" ("V2") Methods with the Current Invention ("V2.X" Alias "Two Step Hydrolysis and Mixed Sugar Hydrolysis")

Figure 2:
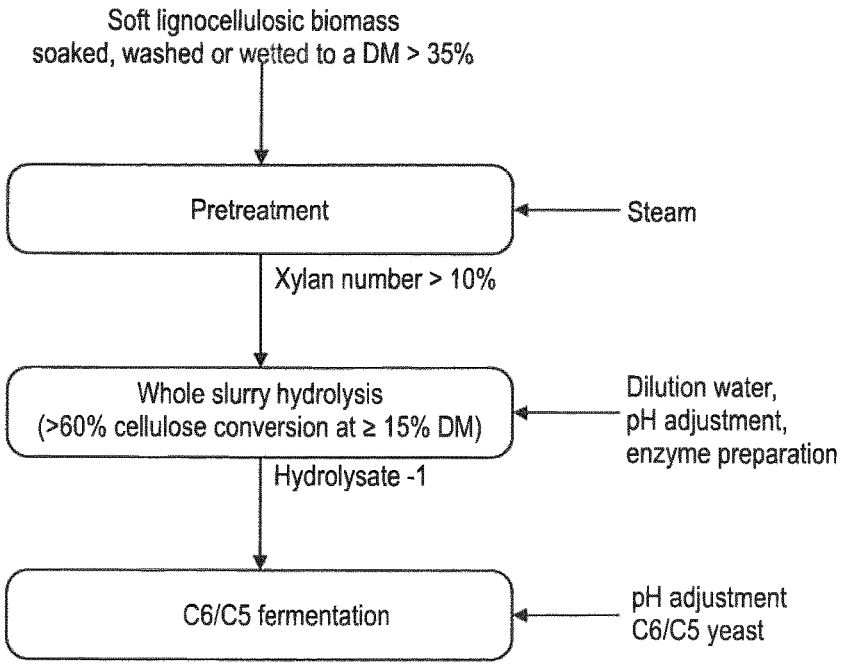
FIG. 2: Process scheme (1) depicts a process scheme of a relatively simple process configuration, such as a "whole slurry" process as described in WO2015/014364.

Process scheme (1) (FIG. 2) shows a relatively simple process configuration, such as a "whole slurry" processes described in WO2015/014364:

1) Biomass, such as soft lignocellulosic biomass, is steam pretreated at low severity (xylan number >10%, such as 10-20%).
2) The pretreated biomass is pH- and temperature-adjusted before enzymatic hydrolysis preferably in a single step hydrolysis process (hence the name whole slurry hydrolysis).
3) After enzymatic hydrolysis, the whole slurry hydrolysate is pH- and temperature-adjusted before fermentation with a suitable microorganism. The whole slurry hydrolysate is the single substrate for microbial fermentation, such as a yeast fermentation providing e.g. EtOH.

Process scheme (2) (FIG. 3) shows a more complex process comprising a "C5 bypass", such as processes described in WO 2014/019589: "Methods of processing lignocellulosic biomass using single-stage autohydrolysis and enzymatic hydrolysis with C5 by-pass and post-hydrolysis":

1) Biomass, such as soft lignocellulosic biomass, is steam pretreated at low severity (xylan number >10%, such as 10-20%).
2) The pretreated biomass is separated (solid/liquid separation process) into a fiber fraction (A) and a liquid fraction (B), said liquid fraction (B) comprising C5 sugars (hence the name "C5 by-pass").
3) The fiber fraction (A) is diluted to a suitable dry matter content (e.g. 15-40% dry matter (DM)), and pH- and temperature-adjusted before enzymatic hydrolysis.
4) The C5-bypass (liquid fraction (B)) is added at some point to the hydrolysing or hydrolysed fiber fraction. It is believed that e.g. hemicellulose-derived oligomers, such as xylan oligomers from the C5 by-pass are degraded to monomers by enzymes as added in the fiber hydrolysis.
5) The final hydrolysate is pH- and temperature-adjusted before fermentation with a suitable microorganism. The final hydrolysate is the single substrate for microbial fermentation, such as a yeast fermentation providing e.g. EtOH.

Process scheme (3) (FIG. 4) depicts examples of a process according to the current invention (also termed "V2.X" (or "two step hydrolysis and mixed sugar hydrolysis")):

1) Lignocellulosic biomass, such as soft lignocellulosic biomass, is steam pretreated at a low severity in a single- or multiple-step pretreatment process; medium or high pretreatment severities comprise other options according to the present invention.
2) The pretreated biomass is separated into a first fiber fraction ("solid fraction-1") and a first liquid fraction ("liquid fraction-1").
3) The fiber fraction (A) is adjusted/diluted to a suitable dry matter content (e.g. 15-40% DM), and pH- and/or temperature-adjusted before enzymatic fiber hydrolysis.
4) The hydrolysed fiber fraction is separated in to a fiber fraction ("solid fraction-2") and liquid fraction ("liquid fraction-2").
5) "Solid fraction-2" is adjusted/diluted to a suitable dry matter content, and pH- and/or temperature-adjusted before enzymatic fiber cake hydrolysis.
6) "Liquid fractions-1 and -2" are combined, and pH- and/or temperature adjusted before hydrolysed with or without addition of additional enzymes (mixed sugar hydrolysis).
7) Optionally, at least a fraction of the mixed sugar hydrolysate can be subjected to ultra-filtration, aiming as recycling at least a fraction of the enzymes, and adding the recycled enzymes to the mixed sugar hydrolysis.
8) Optionally, the fiber cake hydrolysate can be subjected to a further solid/liquid separation step, providing a third fiber fraction ("fiber fraction-3") and a third liquid fraction ("liquid fraction-3")
9) Optionally, the hydrolysates from fiber cake hydrolysis and/or mixed hydrolysis are pH- and/or temperature-adjusted before fermentation with a suitable microorganism, such as a yeast, providing EtOH.

This process provides different hydrolysates with different levels of inhibitors. Thus, there is the option to feed the fermentation from two hydrolysates with different content of inhibiting substances formed in pretreatment, in particular starting a fermentation with the hydrolysate with the lowest concentration of inhibitors.

Figure 4:
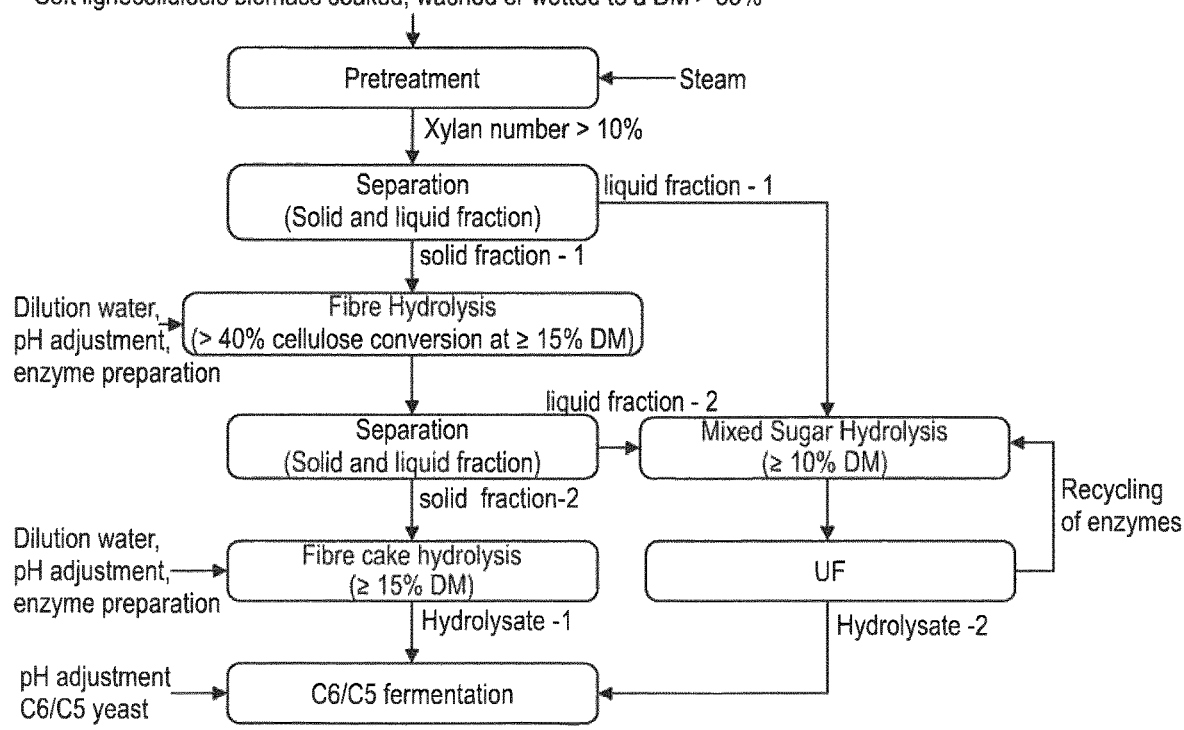
FIG. 4: Process scheme (3) depicts an embodiment/process scheme according to the current invention (also termed "V2.X" or "twostep hydrolysis and mixed sugar hydrolysis" herein).

Furthermore, suitable enzyme preparations, can be added either as enzyme mixes or single enzyme activities at different process steps, such as at (i) fiber hydrolysis, (ii) fiber cake hydrolysis and/or (iii) mixed sugar hydrolysis (see e.g. FIG. 1 or 4). In some embodiments, addition of further enzymes in any one of said steps (ii) and/or (iii) is optional—this may not clearly be depicted in said figures.

"Adjusted/diluted to a suitable dry matter content" before fiber—and/or fiber cake hydrolysis may comprise the addition of water, such as process water.

If available, e.g. when in close vicinity or in combination suitable processing facility providing "raw juice"—i.e. a water-base liquid comprising fermentable sugars, such as a 1 G EtOH processing facility, or a sugar or fruit juice producing facility—said dilution may comprise such a "raw juice".

Advantages of such a combination, such as water savings and/or increased fermentation yields are disclosed in e.g. WO2015/120859, or PCT/EP2016/069775, both applications being herewith incorporated by reference in their entirety.

In summary, and without wanting to be construed as limiting, the present invention may provide, inter alia, one or more of the following effects and/or advantages:

1. increased C5/C6 product yield
2. reduced enzyme consumption
3. addition of enzymes where they are needed
4. water savings
5. cost savings,
6. improved lignin quality
7. increased yield of fermentation product, such as C1-C4 product, such as EtOH
8. reduced need for water Numbered Embodiments Relevant aspects and embodiments of the current invention may also be found in the following section, termed "numbered embodiments".

2. A method for providing a C5/C6 product from a lignocellulosic material comprising the steps:
   a) Pretreatment of the lignocellulosic material;
   b) Solid/liquid separation of the pretreated lignocellulosic material from step (a) into a first solid fraction and a first liquid fraction;
   c) Enzymatic hydrolysis ("fiber hydrolysis") of said first solid fraction from step (b) by use of an enzyme composition capable of degrading lignocellulosic material, thereby providing a "C5/C6 Fiber hydrolysis slurry" comprising C5 and/or C6 sugars;
   d) Solid/liquid separation of the "C5/C6 Fiber hydrolysis slurry" from step (c) into a second solid fraction and a second liquid fraction; and optionally
   e) Combining said first liquid fraction and said second liquid fraction for enzymatic hydrolysis ("Mixed sugar hydrolysis (MSH)"), whereby a "MSH C5/C6 product" is provided.

3. The method according to embodiment 1, comprising step (f): enzymatic hydrolysis ("fiber cake hydrolysis") of said second solid fraction from step (d) to obtain a "slurry C5/C6 product".

4. The method according to embodiment 1 or 2, wherein the lignocellulosic material is soft lignocellulosic biomass.

5. The method according to any one of the preceding embodiments, wherein the pretreatment is conducted at a dry matter (DM) content in the range of 5-80, 10-70, 20-60, 30-50%, and/or at a DM content around 10, 15, 20, 25, 30, 35, 40, 45, 50, 55, 60, 65, 70, 75, 80 or more than 80%.

6. The method according to any one of the preceding embodiments, wherein the pretreatment is conducted at low, medium, or high severity; and/or at conditions providing a xylan number of >10%, 6-10% or <6%.

7. The method according to any one of the preceding embodiments, wherein the enzymatic fiber hydrolysis, fiber cake hydrolysis and/or MSH is/are conducted for a period of at least 6, 12, 24, 48, or 72 h, such as 6-120 h, 12-100 h, or 48-96 h, or around 12, 24, 48, 72, 96, or 120 h.

8. The method according to any one of the preceding embodiments, wherein the enzymatic fiber hydrolysis, fiber cake hydrolysis and/or MSH is/are conducted at a pH in the range of at least pH 3.0, such as 3.0-6.0, 4.0-5.5, 4.2-5.4, and/or around 4.2, 4.5, 4.7, 4.8, 4.9, 5.0, 5.1, 5.2, 5.3 or 5.4.

9. The method according to any one of the preceding embodiments, wherein the enzymatic fiber hydrolysis, fiber cake hydrolysis and/or MSH is/are conducted at a temperature in the range of 30-70° C., 40-65° C., 50-62° C., 55-60° C., and/or around 40, 42, 44, 46, 48, 50, 52, 54, 56, 68, 60, 62, 64, 66, 68, or 70° C.

10. The method according to any one of the preceding embodiments, wherein the enzymatic fiber hydrolysis and/or fiber cake hydrolysis are conducted at suitable DM content, such as a DM content above 10 or 15%, such as around 15-45, 20-40%, 25-35%, and/or around 15, 20, 25, 30, 35, or 40%.

11. The method according to any one of the preceding embodiments, wherein the enzyme composition capable of degrading lignocellulosic material comprises a cellulase and/or a hemicellulase.

12. The method according to any one of the preceding embodiments, wherein the enzyme composition capable of degrading lignocellulosic material comprises a mixture of cellulase(s) and/or hemicellulase(s).

13. The method according to any one of the preceding embodiments, wherein the hemicellulase is or comprises one or more xylanase(s), xylosidase(s), arabinoxylanase(s), xyloglucanase(s), glucoronoxylanase(s), glucomannanase(s), and/or esterase(s), including any combination thereof.

14. The method according to embodiment 12, wherein the esterase(s) is or comprises one or more acetylesterases and/or feroyl esterase.

15. The method according to any one of the preceding embodiments, wherein the enzyme composition capable of degrading lignocellulosic material comprises one or more of endocellulase, endoglucanase, exocellulase, exoglucanase, endoxylanase, acetyl xylan esterase, xylosidase and/or β-glucosidase activities.

16. The method according to any one of the preceding embodiments, wherein step (e) is conducted by combining said first liquid fraction and said second liquid fraction and enzymatically hydrolysing the mixture.

17. The method according to any one of the preceding embodiments, wherein hemicellulase(s) present in step (e) comprises xylanase(s), xylosidase(s), arabinoxylanase(s), xyloglucanase(s), glucoronoxylanase(s), glucomannanase(s), esterase(s), acetylesterases, and/or feroyl esterase(s), including any combination thereof.

18. The method according to any of the preceding embodiments, wherein all or at least a fraction of the hemicellulase(s) used in step (e) has been added in step (c).

19. The method according to any of the preceding embodiments, wherein at least a fraction of the hemicellulase(s) used in step (e) has been added in step (c).

20. The method according to any one of the preceding embodiments, wherein one or more hemicellulase(s) is/are added in step (e).

21. The method according to any one of the preceding embodiments, wherein one or more additional enzyme(s) is provided in step (e).

22. The method according to embodiment 20, wherein the additional enzyme(s) is essentially not present in the enzyme composition capable of degrading lignocellulosic material used/provided in step (c).

23. The method according to embodiment 20 or 21, wherein the additional enzyme(s) is one or more of: hemicellulase(s), xylanase(s), xylosidase(s), arabinoxylanase(s), xyloglucanase(s), glucoronoxylanase(s), glucomannanase(s), esterase(s), acetylesterases, and/or feroyl esterase(s), including any combination thereof.

24. The method according to any of the preceding embodiments, wherein step (e) comprises an ultrafiltration step (j) for recycling enzymes present after MSH.

25. The method according to embodiment 23, wherein the ultrafiltration step (j) is adapted to allow for recycling of at least 30, 50, 75, 80, or 90% (w/w) of the enzyme activity.

26. The method according to any of the preceding embodiments, wherein all the cellulase used in step (f) has been added in step (c).

27. The method according to any of the preceding embodiments, wherein at least a fraction of the cellulase used in step (f) has been added in step (c).

28. The method according to any one of the preceding embodiments, wherein one or more cellulase(s) and optionally hemicellulase(s) is/are added in step (f).

29. The method according to any one of the preceding embodiments, wherein the MSH and/or fiber cake hydrolysis are performed without addition of one or more enzyme(s).

30. The method according to any one of the preceding embodiments, wherein the MSH and/or fiber cake hydrolysis are performed without addition of one or more cellulase and/or one or more hemicellulase.

31. The method according to any one of the preceding embodiments further comprising the step: g) Solid/liquid separation of the "slurry C5/C6 product" from step (f) into a third solid fraction and a third liquid fraction ("liquid C5/C6 product").

32. The method according to any one of the preceding embodiments, wherein the second liquid fraction possesses a lower inhibitor concentration than the first liquid fraction.

33. The method according to any one of the preceding embodiments, wherein the second liquid fraction possesses a lower inhibitor concentration than the "MSH C5/C6 product".

34. The method according to any one of the preceding embodiments, wherein the "slurry C5/C6 product" possesses a lower inhibitor concentration than the "MSH C5/C6 product".

35. The method according to any one of the preceding embodiments, further comprising the step: K) Combining at least a portion of the "MSH C5/C6" product with at least a portion of one or more of: the "slurry C5/C6 product" from step (f), the "liquid C5/C6 product" from step (g), and/or the second liquid fraction from step (d) to obtain a "combined C5/C6 product".

36. The method according to embodiment 34, wherein the "combined C5/C6 product" consists or consists essentially of the "MSH C5/C6" product and the "slurry C5/C6 product" from step (f); the "MSH C5/C6" product and the "liquid C5/C6 product" from step (g); or the "MSH C5/C6" product and the second liquid fraction from step (d).

37. The method according to any one of the preceding embodiments, further comprising a lignin recovery step, such as a removal of water, compacting and/or pelleting.

38. The method according to embodiment 36, wherein said lignin recovery is conducted on the second or third solid fraction provided in steps (d) or (g).

39. The method according to any one of the preceding embodiments, wherein any C5/C6 product is a C5+C6 product, i.e. a product comprising C5 and C6 carbohydrates, such as xylose and glucose, including structural analogues, isomers and/or derivatives thereof.

40. The method according to any one of the preceding embodiments, wherein the C5+C6 product comprises glucose and xylose.

41. A method for providing a fermentation product, said method comprising the steps of:
    m) Providing at least one C5/C6 product according to the method of any one of the preceding embodiments; and
    n) Providing the fermentation product by a fermentation of said C5/C6 product with a microorganism.

42. The method according to embodiment 40, wherein the C5/C6 product is or comprises one or more of: "MSH C5/C6 product", "Slurry C5/C6 product", "Liquid C5/C6 product", "Combined C5/C6 product, first liquid fraction, or second liquid fraction, including any combination thereof.

43. The method according to embodiment 40 or 41 wherein the fermentation product is provided in a fermentation broth, said method further comprising the step: (o) recovering said fermentation product from a fermentation broth.

44. The method according to any one of embodiments 40-42, further comprising the step: (p) recovering lignin from a spent fermentation broth, and/or a fraction provided in step (n) or (o).

45. The method according to embodiment 43, wherein fermentation is carried in at least two subsequent fermentation steps ("first and a second fermentation"), wherein a first and a second fermentation substrate are fermented.

46. A two-step fermentation method comprising the steps of:
    aa) Pretreatment of the lignocellulosic material;
    bb) Solid/liquid separation of the pretreated lignocellulosic material from step (a) into a first solid fraction and a first liquid fraction;
    cc) Enzymatic hydrolysis ("fiber hydrolysis") of said first solid fraction from step (b) by use of an enzyme composition capable of degrading lignocellulosic material, thereby providing a "C5/C6 Fiber hydrolysis slurry";
    dd) Solid/liquid separation of the "C5/C6 Fiber hydrolysis slurry" from step (cc) into a second solid fraction and a "second liquid fraction";
    ee) Enzymatic hydrolysis ("mixed sugar hydrolysis" MSH) of a mixture of the first liquid fraction from step (bb) and the "C5/C6 fiber hydrolysis slurry" from step (cc), or the first liquid fraction from step (bb) and the second liquid fraction from step (dd), thereby providing a "C5/C6 MSH product";
    ff) Providing a first fermentation substrate comprising at least a portion of the "C5/C6 fiber hydrolysis slurry" and/or the second liquid fraction;
    gg) Providing a second fermentation substrate comprising at least a portion of the C5/C6 MSH product;
    hh) Fermenting the first fermentation substrate in a first fermentation with a microorganism; and
    ii) Fermenting the second fermentation substrate in a subsequent second fermentation;
    wherein step (dd) is optional.

47. The method according to any one of embodiments 44 or 45, wherein the first fermentation substrate possesses a significantly lower inhibitor concentration than the second fermentation substrate.

48. The method according to any one of embodiments 44-46, wherein the first fermentation is a batch or fed-batch fermentation.

49. The method according to any one of embodiments 44-47, wherein the first fermentation is carried out by providing a first fermentation substrate comprising:
    x. the second liquid fraction provided in step (d) or (dd);
    y. "C5/C6 fiber hydrolysis slurry" provided in step (c) or (cc); and/or
    z. the C5/C6 product obtained in step (f), i.e. the "liquid C5/C6 product" or the "slurry C5/C6 product".

50. The method according to any one of embodiments 44-48, wherein the first fermentation is carried out by providing a first fermentation substrate consisting essentially of:
    x. the second liquid fraction provided in step (d) or (dd);
    y. "C5/C6 fiber hydrolysis slurry" provided in step (c) or (cc); and/or
    z. the C5/C6 product obtained in step (f), i.e. the "liquid C5/C6 product" or the "slurry C5/C6 product".

51. The method according to any one of embodiments 44-49, wherein the first fermentation substrate comprises or consists essentially of a mixture of the second liquid fraction and the C5/C6 product obtained in step (f), i.e. the "liquid C5/C6 product" or the "slurry C5/C6 product".

52. The method according to embodiment 50, wherein the ratio of the second liquid fraction and the C5/C6 product is in the range of 100:0.1-0.1:100, 10:0.1-0.1:10, or 10:1-1:10 (w/w); or around 50:1, 25:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:25, 1:50 (w/w).

53. The method according to any one of embodiment 44-51, wherein the first fermentation substrate is provided essentially without dilution with process water.

54. The method according to any one of embodiments 44-52, wherein the second fermentation is a fed-batch fermentation or a continuous fermentation, optionally conducted in the same fermenter as the first fermentation.

55. The method according to any one of embodiments 44-53, wherein the fed-batch fermentation is with linear or exponential feed.
56. The method according to any one of embodiments 44-54, wherein the second fermentation is conducted with the same microorganisms as in the first fermentation.
57. The method according to any one of embodiments 44-55, wherein the second fermentation is carried out by providing a second fermentation substrate comprising or consisting essentially of a mixture of the C5/C6 product obtained in step (f) (i.e. the "liquid C5/C6 product" or "slurry C5/C6 product") and the C5/C6 product obtained from step (e) (i.e. "MSH C5/C6 product").
58. The method according to embodiment 56, wherein the ratio of the "liquid C5/C6 product" or "slurry C5/C6 product") and the C5/C6 product obtained from step (e) (i.e. "MSH C5/C6 product") is in the range of 100:0.1-0.1:100, 10:0.1-0.1:10, or 10:1-1:10, 5:1-1:5; 4:1-1:4, 3:1-1:3, 2.5-1:2.5, 2:1-1:2 or 1.5-1:1-1.5 (w/w); or around 50:1, 25:1, 20:1, 15:1, 10:1, 9:1, 8:1, 7:1, 6:1, 5:1, 4:1, 3:1, 2:1, 1:1, 1:1.5, 1:2, 1:2.5, 1:3, 1:4, 1:5, 1:6, 1:7, 1:8, 1:9, 1:10, 1:15, 1:20, 1:25, 1:50 (w/w).
59. The method according to any one of embodiments 44-57, wherein the second fermentation is carried out by providing a second fermentation substrate comprising or consisting essentially of the C5/C6 MSH product provided in step (ee).
60. The method according to any one of embodiments 44-58, wherein the second fermentation is provided essentially without dilution with of process water.
61. The method according to any one of embodiments 44-59, wherein the volume of the first fermentation is significantly smaller than the volume of the second fermentation.
62. The method according to embodiment 60, wherein the volume of the first fermentation is 2-40%, 3-30%, 5-20%, 7.5-15%, 8-12%, or around 10% of the volume of the second fermentation.
63. The method according to any one of embodiments 40-61, wherein the fermentation product is recovered by distillation.
64. The method according to any one of embodiments 40-62, wherein the fermentation product is EtOH.
65. The method according to embodiment 62 or 63, further comprising a lignin recovery step from a distillation remnant.
66. The method according to any one of embodiments 44-64, wherein the first and second fermentation are consecutive fermentations, optionally conducted in the same fermenter.
67. The method according to any one of embodiments 44-65, wherein the second fermentation comprises fermentation of both the first liquid fraction and the "C5/C6 Fiber hydrolysis slurry".
68. The method according to any one of embodiments 40-66, wherein the fermentation product is an alcohol, organic acid, vitamin, amino acid, peptide, enzyme or the like.
69. The method according to any one of embodiments 40-67, wherein the fermentation product is a C1-C4 product.
70. The method according to embodiment 68, wherein the C1-C4 product is one or more of: methanol, ethanol, butanol, acetone, formic acid, acetic acid, propionic acid, butyric acid, oxalic acid, lactic acid, malic aid, and/or any combination thereof.
71. The method according to embodiment 68 or 69, wherein the C1-C4 product is EtOH.
72. The method according to any one of embodiments 40-70, wherein the microorganism is a eukaryotic or prokaryotic microorganism, such as a bacterium or a yeast.
73. The method according to any one of embodiments 40-71, wherein the microorganism is a recombinant microorganism.
74. The method according to any one of embodiments 40-72, wherein microorganism is capable of fermenting C5 and C6 sugars, such as xylose and glucose.
75. The method according to any one of embodiments 40-73, wherein microorganism is a yeast, such as a *Saccharomyces cerevisiae* capable of or adapted to fermenting xylose and glucose to EtOH.
76. A method for preparing ethanol and optionally lignin from a lignocellulosic material comprising the steps of:
   Providing at least one C5/C6 product according to a method according to any one of the preceding embodiments;
   Fermentation of said at least one C5/C6 product to convert sugars to ethanol in the fermentation broth with a yeast;
   Isolation of an ethanol rich fraction from the fermentation broth; and optionally
   Isolation of lignin.
77. The method according to embodiment 75, wherein the fermentation is conducted according to a method according to any one of embodiments 40-74.
78. The method according to embodiment 75 or 76, wherein the lignin is isolated from the spent fermentation broth or from the remnants from the spent fermentation broth after isolating the ethanol rich fraction.
79. Lignin provided from lignocellulosic biomass according to any one of the preceding embodiments.
80. A C5/C6 product provided according to any one of the preceding embodiments.
81. A fermentation substrate comprising a C5/C6 product provided by a method according to any one of the preceding embodiments.
82. The first or second fermentation substrate provided by a method according to any one of the preceding embodiments.
83. Use of lignin according to embodiment 78 in a bitumen composition, such as asphalt.
84. A composition comprising 0.1-99.9% (w/w) lignin according to embodiment 78.
85. A bitumen composition comprising:
   a. 1-99.89% (w/w) bitumen;
   b. 0.1-50% (w/w) lignin according to embodiment 78;
   c. 0.01-20% (w/w) plasticity modifying agent(s); and
   d. 0-95% (w/w) further component(s).
86. The bitumen composition according to embodiment 84, wherein the plasticity modifying agent is one or more plastomer, one or more thermoplastic elastomer, one or more rubber, one or more viscosity modifier, and/or one or more reactive polymer, including any combination thereof.
87. The bitumen composition according to embodiment 84 or 85, wherein the further component(s) is one or more dispersing agent(s), surfactant(s), hydrotropic agent(s), emulsifier(s), preserving agent(s), anti-foaming agent(s), viscosity modifier(s), reactive polymer(s)

and any combination thereof; and/or one or more aggregate(s) and/or filler(s), such natural, manufactured, recycled aggregates, including any combination thereof.

88. A composition comprising 0.1-99.9% (w/w) lignin according to embodiment 78.
89. Use of a composition according to any one of embodiments 83-87 in sealing work, road work, paving work, providing a surface layer, providing a sealing layer, providing a road and providing a pavement, providing a top layer of a road
90. Use of a composition according to any one of embodiments 83-87 in applications relating to (i) agriculture, (ii) buildings and industrial paving, (iii) hydraulics and erosion control, (iv) industrial, (v) paving, (vi) railways, and (vii) recreation, such as ad (i) disinfectants, fence post coating, mulches, mulching paper, paved barn floors, barnyards, feed platforms, protecting tanks, vats, protection for concrete structures, tree paints (protective); ad (ii): water and moisture barriers (above and below ground), floor compositions, tiles, coverings, insulating fabrics, papers, step treads, building papers, caulking compounds, cement waterproofing compounds, glass wool compositions, insulating fabrics, felts, papers, joint filler compounds, laminated roofing shingles, liquid roof coatings, plastic cements, shingles, acoustical blocks, compositions, felts, bricks, damp-proofing coatings, compositions, insulating board, fabrics, felts, paper, masonry coatings, plasterboards, putty, soundproofing, stucco base, wallboard, air-drying paints, varnishes, artificial timber, ebonised timber, insulating paints, plumbing, pipes, treated awnings, canal linings, sealants; ad (iii): catchment areas, basins, dam groutings, dam linings, protection, dyke protection, ditch linings, drainage gutters, structures, embankment protection, groynes, jetties, levee protection, mattresses for levee and bank protection, membrane linings, waterproofing, reservoir linings, revetments, sand dune stabilisation, sewage lagoons, oxidation ponds, swimming pools, waste ponds, water barriers, backed felts, ad (iv): conduit insulation, lamination, insulating boards, paint compositions, papers, pipe wrapping, insulating felts, panel boards, underseal, battery boxes, carbons, electrical insulating compounds, papers, tapes, wire coatings, junction box compound, moulded conduits, black grease, buffing compounds, cable splicing compound, embalming, etching compositions, extenders, explosives, lap cement, plasticisers, preservatives, printing inks, well drilling fluid, armoured bituminised fabrics, burlap impregnation, mildew prevention, sawdust, cork, asphalt composition, acid-proof enamels, mastics, varnishes, acid-resistant coatings, air-drying paints, varnishes, anti-corrosive and anti-fouling paints, anti-oxidants and solvents, base for solvent compositions, baking and heat-resistant enamels, boat deck sealing compound, lacquers, japans, marine enamels, blasting fuses, briquette binders, burial vaults, casting moulds, clay articles, clay pigeons, expansion joints, flowerpots, foundry cores, friction tape, gaskets, mirror backing, rubber, moulded compositions, shoe fillers, soles; ad (v): airport runways, taxiways, aprons, asphalt blocks, brick fillers, bridge deck, surfacing, crack fillers, floors for buildings, warehouses, garages, highways, roads, streets, shoulders, kerbs, gutters, drainage ditches, parking lots, driveways, Portland cement concrete underseal, roof-deck parking, pavements, footpaths, soil stabilisation; ad (vi) ballast treatment, dust laying, paved ballast, sub-ballast, paved crossings, freight yards, station platforms; and ad (vii) dance pavilions, drive-in movies, gymnasiums, sport arenas, playgrounds, school yards, race tracks, running tracks, skating rinks, swimming and wading pools, tennis courts, handball courts, synthetic playing fields and running track surfaces.

EXAMPLES

General Methods and Materials Used in Examples

In this part, the general methods and materials used for the examples presented in this application are described. If deviated from the general methods and materials, this will be specified in the example.

Pretreatment

Pretreatment was conducted in Inbicon's pilot plant, Skærbæk, Denmark. Wheat straw (WS) was soaked in water, pH>4.0, prior to pretreatment at approximately 40% dry matter (DM). About 50 kg DM/h of biomass was pretreated at temperatures from 180-200° C. with a residence time of approximately 18 minutes. The biomass was loaded into the reactor using a sluice system (WO2010/058285) and the pretreated material unloaded again using a sluice system. The pressure within the pressurized pretreatment reactor corresponded to the pressure of saturated steam at the temperature used. The pretreated biomass was subject to solid/liquid separation using a screw press, producing a liquid fraction ("C5 bypass", "first liquid fraction") and a solid fraction ("first solid fraction") with a DM content of approximately 60%. The pretreatment process is further described in Petersen et al. (2009).

Analytical Measurement of Pretreatment Fractions

Raw feedstocks were analysed for carbohydrates according to the methods described in Sluiter et al. (2005) and Sluiter et al. (2008) using a Dionex Ultimate 3000 HPLC system equipped with a Rezex Monossacharide H+ column from Phenomenex.

Samples of liquid fraction and solid fraction were collected after three hours of continuous pretreatment and samples were collected three times over three hours to ensure that a sample was obtained from steady state pretreatment.

The solid fractions were analysed for carbohydrates according to the methods described in Sluiter et al. (2008) with an Ultimate 3000 HPLC system from Dionex equipped with a Rezex Monossacharide H+ Monosaccharide column from Phenomenex.

The liquid fractions were analysed for carbohydrates and degradation products according to the methods described in Sluiter et al. (2006) with an Ultimate 3000 HPLC system from Dionex equipped with a Rezex Monossacharide H+ Monosaccharide column from Phenomenex.

The total solids content (TS), hereafter termed dry matter was measured by drying, approximately 24 hours, until constant weight at 105° C. The suspended solids (SS) were analysed with a method adapted from the methods described in Weiss et al. (2009) by analysing TS of the sample and TS in a sample filtered through a paper filter and calculating the SS amount.

Mass balances were set up as described in Petersen et al. (2009) and cellulose and hemicellulose recoveries were determined.

Hydrolysis

Hydrolysis experiments were conducted in Inbicon's pilot plant, Skærbæk, Denmark in two scales. Fiber hydrolysis experiments were conducted in 10 kg scale in a free fall reactor as described in WO2006/056838. The reactor is designed to conduct experiments with a suspended dry matter content above 20%. The reactor consists of a horizontally placed drum divided into 6 chambers, each 24 cm wide and 50 cm in height. A horizontal rotating shaft mounted with three paddles in each chamber is used for mixing/agitation. A 1.1 kW motor is used as a drive and the rotational speed is adjustable within the range of 2.5 and 16.5 rpm. The direction of rotation is programmed to shift every second minute between clock and anti-clockwise. A water-heated jacket on the outside of the chambers enables temperature control up to 80° C.

Hydrolysis experiments are conducted by adding fiber fraction corresponding to 2.2 kg of suspended solids to a chamber and then adding water or liquid fraction until the desired separation degree of dissolved solids between the fiber and liquid fraction is obtained in order to simulate a full-scale process. The temperature is adjusted to 50° C. The pH is adjusted to the optimal pH for the used enzyme by use of $Ca(OH)_2$ prior to addition of enzymes. The enzymes are added. Stirring is conducted at 6 rpm. After liquefaction, the experiments were transferred to shake flasks. The experiments are sampled after 4 hours and every 24 hours by sampling and diluting ten-fold and analysing according to Kristensen et al. (2009) with an Ultimate 3000 HPLC system from Dionex equipped with a Rezex Monossacharide H+ column from Phenomenex.

Separation in Between Fiber Hydrolysis and Fiber Cake Hydrolysis

After hydrolysis, the slurry was separated into a second fiber fraction, fiber fraction-2, and a second liquid fraction, liquid fraction-2, by pressing in a filter chamber press using one cassette with Tetex Mono V05-1001-SK025 polypropylene filter cloth at 60 to 65° C. for ten minutes at 5 bars feeding pressure and 13 bars pressing pressure.

Materials

Materials used are listed below in Table 1.

TABLE 1

List of materials

| Compound | Manufacturer |
| --- | --- |
| Pretreated wheat straw fibers and liquid fraction | Inbicon |
| Enzyme: Cellic ® CTec3 | Novozymes |
| $Ca(OH)_2$ | Sigma |

Example 1—Comparison of Total Carbohydrate Conversion in the V2.X Method and the V2 (C5 by-Pass) Method An example of the V2.X process is shown in process scheme 3 (FIG. 4). The main hypothesis behind the formation of the V2.X process is—without wanting to be bound to any theory—that significant and probably major parts of cellulases will follow the fibers and main parts of the hemicellulases will follow the liquid phase. Cellulases will be 'reused' in a second fiber hydrolysis step and hemicellulases will be reused in the mixed sugar hydrolysis for hydrolysis of xylo- and other hemicellulose-oligomers found in the liquid fraction-1 and liquid fraction-2. As an option, ultra-filtration (UF) can be used to up-concentrate the enzymes in the mixed sugar hydrolysis and/or to improve hydrolysis yield. The fermentation process takes advantage of and is becoming more efficient when using the two hydrolysates with different content of inhibiting substances in the optimal way.

Differences between the V2.X process (e.g. process scheme 3) and the V2 or the C5 by-pass process (process scheme 2, FIG. 3) comprise introduction of a two-step hydrolysis and/or that mixed sugar hydrolysis is conducted without fibers.

Figure 5:
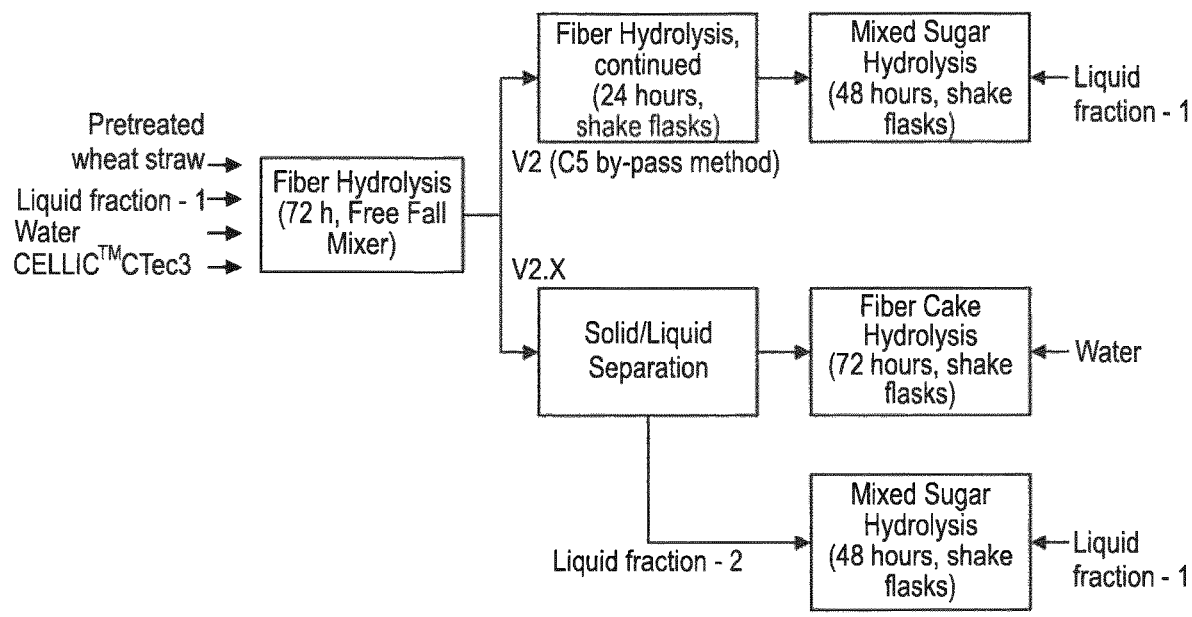
FIG. 5: Experimental design for comparison of total carbohydrate conversion in the V2 and V2.X method.

In an experimental study, the glucan and xylan conversions in the V2.X method and the C5 by-pass method have been compared (FIG. 5). The first 72 hours of fiber hydrolysis is the same for the V2.X method and the C5 by-pass method. The first 72 hours of fiber hydrolysis was conducted in 10 kg scale in a free fall mixer. After 72 hours of fiber hydrolysis, the slurry was split into two fractions, a fraction to be used for continuing with V2.X method and another fraction to be used for continuing with the C5 by-pass method.

Fiber Hydrolysis for the V2.X Method and the C5 by-Pass Method:

The fiber fraction was added to the chambers of the free-fall reactor and water was added to reach a suspended dry matter content of 22 wt-% giving a total dry matter content of 25 wt-%. The pH was adjusted to 5.3 and the temperature to 50° C. The agitator in the free fall mixer was set to 6 rpm. Five chambers were used to compare the V2.X method and the C5 by-pass method.

Table 2 shows the enzyme dosages used. After 72 hours at 50° C. and pH adjusted in the range from 4.8-5.3, the fiber hydrolysis was stopped.

TABLE 2

Enzyme dosages and SS for fiber hydrolysis experiments

| Experiment | Enzyme dosage [g Cellic ® CTec3/kg glucan in FH] | Suspended dry matter [wt % SS] |
| --- | --- | --- |
| 16-13-R6-2 | 50 | 22 |
| 16-13-R6-3 | 40 | 22 |
| 16-13-R6-4 | 75 | 22 |
| 16-13-R6-5 | 50 | 22 |
| 16-13-R6-6 | 40 | 22 |

C5 by-Pass Method

The fraction to continue with C5 by-pass method was transferred to shake flasks, which were placed in a shaking incubator for 24 hours at 50° C. After 24 hours, the C5 bypass (see section "pretreatment" above) was added and the hydrolysis was continued for 50 hours without addition of enzymes. Table 3 shows the enzyme dosages and the suspended dry matter (wt % SS) used.

TABLE 3

Enzyme dosages and suspended dry matter (SS) for mixed sugar hydrolysis (MSH) with V2 or C5 by-pass method

| Experiment | Enzyme dosage [g Cellic ® CTec3/kg glucan in FH] | Suspended dry matter [wt % SS] |
| --- | --- | --- |
| 16-13-R6-2-FE-12-3 | 50 | 17 |
| 16-13-R6-3-FE-12-4 | 40 | 17 |
| 16-13-R6-4-FE-12-5 | 75 | 17 |

TABLE 3-continued

Enzyme dosages and suspended dry matter (SS) for mixed sugar hydrolysis (MSH) with V2 or C5 by-pass method

| Experiment | Enzyme dosage [g Cellic ® CTec3/kg glucan in FH] | Suspended dry matter [wt % SS] |
|---|---|---|
| 16-13-R6-4-FE-12-6 | 75 | 17 |
| 16-13-R6-5-FE-12-7 | 50 | 17 |
| 16-13-R6-6-FE-12-8 | 40 | 17 |

V2.X Method

The slurry fraction that continued in the V2.X method was pressed into a fiber cake and a filtrate as described above. The fiber cakes were allocated to six shake flasks and re-suspended in water. Fiber cake hydrolysis was conducted for 72 hours with enzyme dosages and SS % as shown in Table 4. The filtrate fraction was transferred to shake flasks and the C5 bypass was added to start the mixed sugar hydrolysis, which had a retention time of 48 hours. Table 5 shows the enzyme dosage and % SS in the MSH. Both the fiber cake hydrolysis and the MSH were conducted at 50° C. and pH 5.0-5.3. The agitation for the fiber cake hydrolysis and the MSH were set to 250 rpm in the shaking incubator, see also FIG. 5 for an overview of the setup.

TABLE 4

Enzyme dosages and SS for fiber cake hydrolysis with V2.X method

| Experiment | Enzyme dosage [g Cellic ® CTec3/kg glucan in FH] | Suspended dry matter [wt % SS] |
|---|---|---|
| 16-13-R6-2-FE-13-14 | 50 | 19 |
| 16-13-R6-3-FE-13-17 | 40 | 19 |
| 16-13-R6-4-FE-13-20 | 75 | 18 |
| 16-13-R6-5-FE-13-23 | 50 | 19 |
| 16-13-R6-6-FE-13-26 | 40 | 18 |

TABLE 5

Enzyme dosages and SS for MSH with V2.X method

| Experiment | Enzyme dosage [g Cellic ® CTec3/kg glucan in FH] | Suspended dry matter [wt % SS] |
|---|---|---|
| 16-13-R6-2-FE-13-28 | 50 | 0 |
| 16-13-R6-3-FE-13-29 | 40 | 0 |
| 16-13-R6-4-FE-13-30 | 75 | 0 |
| 16-13-R6-5-FE-13-31 | 50 | 0 |
| 16-13-R6-6-FE-13-32 | 40 | 0 |

Results

Figure 6:
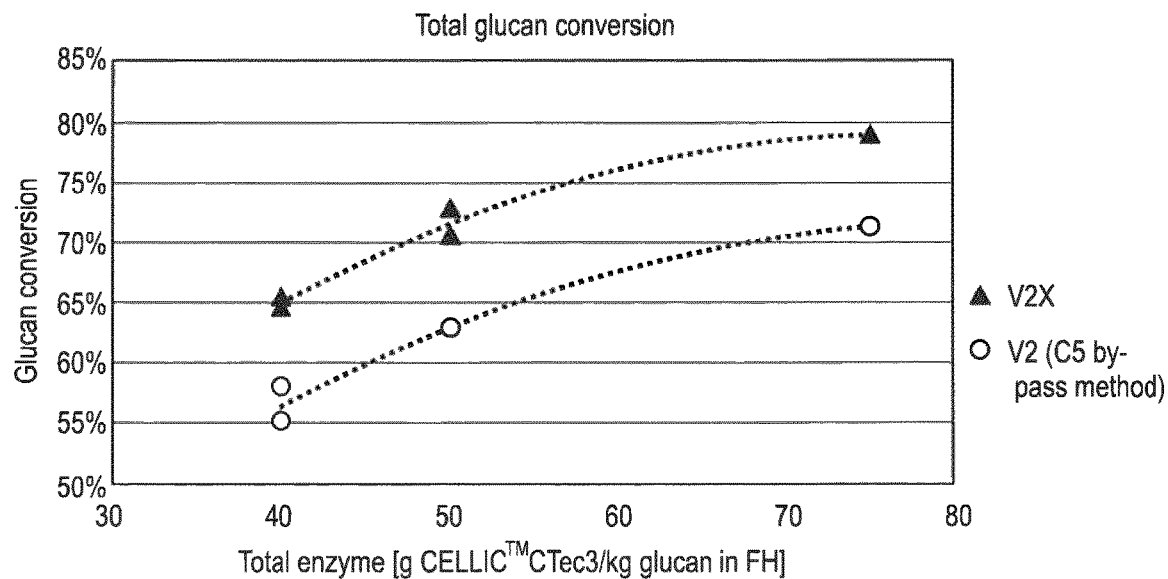
FIG. 6: Glucan conversion as a function of enzyme dose for the V2.X, V2 and C5 bypass method with lines to guide the eye.
Figure 7:
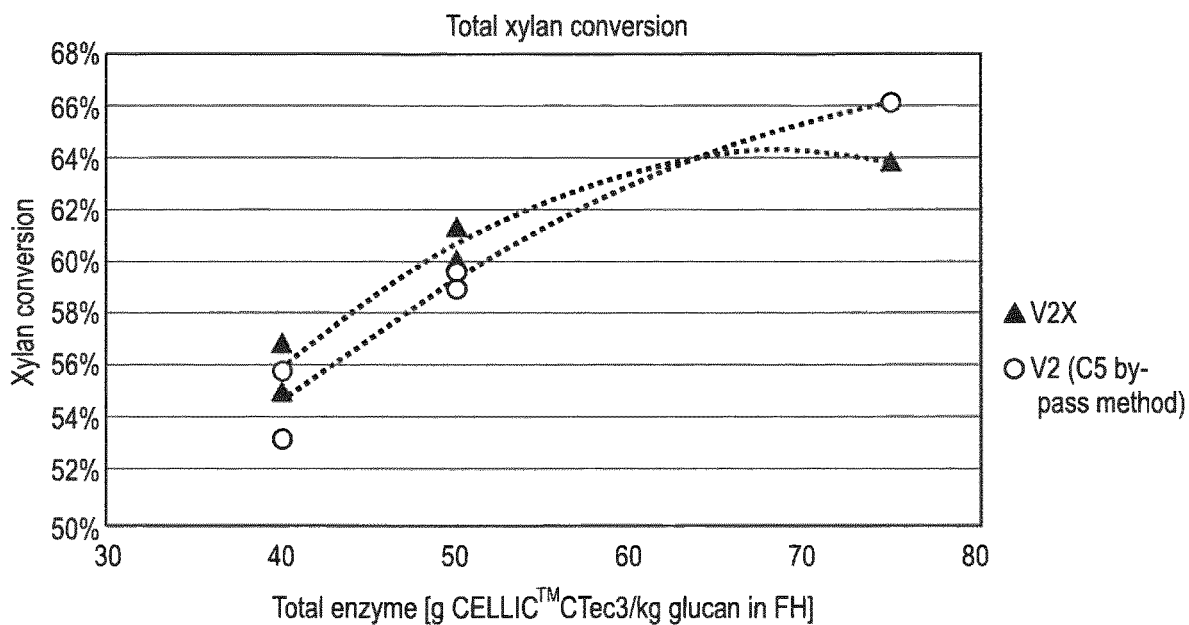
FIG. 7: Xylan conversion as a function of enzyme dose for the V2.X and the C5 by-pass method with lines to guide the eye.
Figure 8:
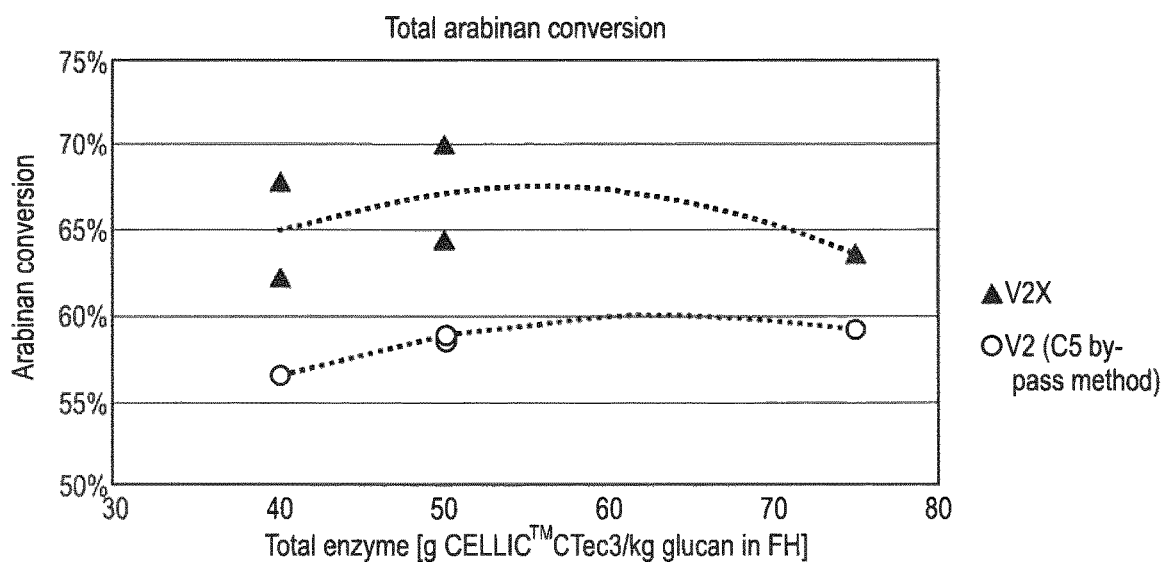
FIG. 8: Arabinan conversion as a function of enzyme dose for the V2.X method and C5 by-pass method with lines to guide the eye.

After all the hydrolysis were conducted, the sugar concentrations were measured and mass balances were calculated. The glucan, xylan and arabinan conversions were calculated as sum of glucose, xylose and arabinose after mixed sugar hydrolysis and fiber cake hydrolysis divided by the sum of glucan, xylan and arabinan respectively in the fiber fraction and the C5-bypass. The glucan conversion calculated based on total amount of glucan from pretreatment increases with 11-17% (relatively), when using the V2.X method compared to the C5 by-pass method, see FIG. 6. The xylan conversion calculated based on total amount of xylan from pretreatment is similar respectively for the V2.X method and the C5 by-pass method, which confirms that most of the xylanases follow the filtrate after the press of the slurry from the fiber hydrolysis (FIG. 7). The arabinan conversion calculated based on total amount of arabinan from pretreatment increases with 7 to 19% (relatively) when using the V2.X method compared to the C5 by-pass method, which shows that other hemicellulases than xylanases follow the filtrate (FIG. 8).

Conclusion

Hydrolysis experiments were conducted in 10 kg scale at industrial relevant dry matter with three different enzyme dosages to compare the V2 (C5 by-pass method) and the V2.X method. In all experiments, better yields were obtained for overall monomeric carbohydrate yield in the V2.X method. The average increase observed was 8% more absolute conversion of glucan to glucose, no significant change in conversion of xylan to xylose is observed and 7% more absolute conversion of arabinan to arabinose.

Example 2—Comparison of Carbohydrate Conversion of the Fiber Fraction in the V2.X Method and the V2 (C5 by-Pass) Method with Multiple Pretreatments and Biomasses The V2.X process was tested with different wheat straw batches and different pretreatments (see also Table 6). The comparison between the V2.X method and the V2 or C5 by-pass method was based on the enzymatic conversion of the fiber fractions. The total enzyme dose to fiber fraction was similar; 75 g Cellic® CTec3/kg total glucan in FH. The enzyme was added in one portion to the fiber hydrolysis in the C5 by-pass method while added in two steps distributed to fiber and fiber cake hydrolysis in the V2.X method. In both cases, no mixed sugar hydrolysis was conducted. Comparison of mixed sugar hydrolysis in both methods is described in example 5.

Fiber Hydrolysis for the C5 by-Pass Method:

The fiber fraction was added to the chambers of the free-fall reactor and water added to reach a SS of 22 wt % giving a total dry matter content of 25 wt %. The pH was adjusted to 5.3 and the temperature to 50° C. The agitator in the free-fall mixer was set to 6 rpm. After approx. 100 hours at 50° C. and pH adjusted in the range from 4.8-5.3 the fiber hydrolysis was stopped. In one case (16-13-R6-4), the fiber mash was removed from the free-fall reactor after 72 h and fiber hydrolysis was continued in shake flasks for another 24 h.

TABLE 6

Enzyme dosage for fiber hydrolysis experiment with C5 by-pass method

| Wheat straw batch | Pretreatment experiment | Hydrolysis experiment | Enzyme dosage [g Cellic ® CTec3/kg glucan in FH] |
|---|---|---|---|
| WS_F | WS_F_20150729 | 15-71-R6-1 | 75 |
| WS_F | WS_F_20150902 | 15-71-R6-2 | 75 |
| WS_F | WS_F_20150923 | 16-4-R6-4 | 75 |
| WS_F | WS_F_20140828 | 16-4-R6-2 | 75 |
| WS_H | WS_H_20160203 | 16-13-R6-4 | 75 |

Fiber and Fiber Cake Hydrolysis for the V2.X Method:

The fiber fraction was added to the chambers of the free-fall reactor and water added to reach a SS of 22 wt-% giving a total dry matter content of 25 wt-%. The pH was adjusted to 5.3 and the temperature to 50° C. The enzyme dosage for this experiment is given in Table 7. The agitator in the free fall mixer was set to 6 rpm. After approx. 72 hours at 50° C. and pH adjusted in the range from 4.8-5.3 the fiber hydrolysis was stopped. The slurry was pressed into a fiber cake and filtrate as previously described. The fiber cakes were allocated to five shake flasks and re-suspended in water and the second portion of enzymes was added. The fiber cake hydrolysis was conducted for 68 to 72 hours at 50° C. and pH 5.0-5.3. The agitation for the fiber cake hydrolysis was set to 250 rpm in the shaking incubator.

TABLE 7

Enzyme dosages for fiber and fiber cake hydrolysis with V2.X method

| Wheat straw batch | Pretreatment experiment | Hydrolysis experiment | Enzyme dosage, Fiber Hydrolysis | Enzyme dosage, Fiber Cake Hydrolysis |
|---|---|---|---|---|
| | | | [g Cellic ® CTec3/kg glucan in FH] | |
| WS_F | WS_F_20150729 | 15-78-R6-1-FE-48-1/2/11/12 | 50 | 25 |
| WS_F | WS_F_20150902 | 15-78-R6-2-FE-48-3/4 | 50 | 25 |
| WS_F | WS_F_20150923 | 15-78-R6-4-FE-48-5/6 | 50 | 25 |
| WS_F | WS_F_20140828 | 15-78-R6-5-FE-48-7/8 | 50 | 25 |
| WS_H | WS_H_20160203 | 16-13-R6-2/5-FE-13-4/13 | 50 | 25 |

Results

Figure 9:
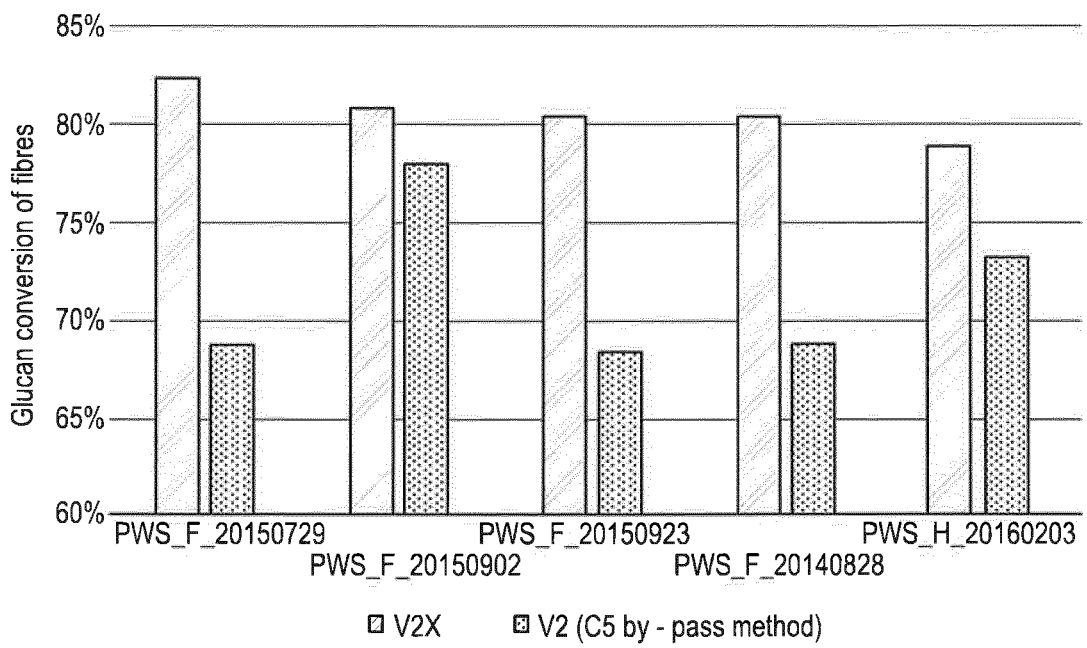
FIG. 9: Glucan conversion of fibers for V2.X and the C5 by-pass method for five different pretreatment dates.
Figure 10:
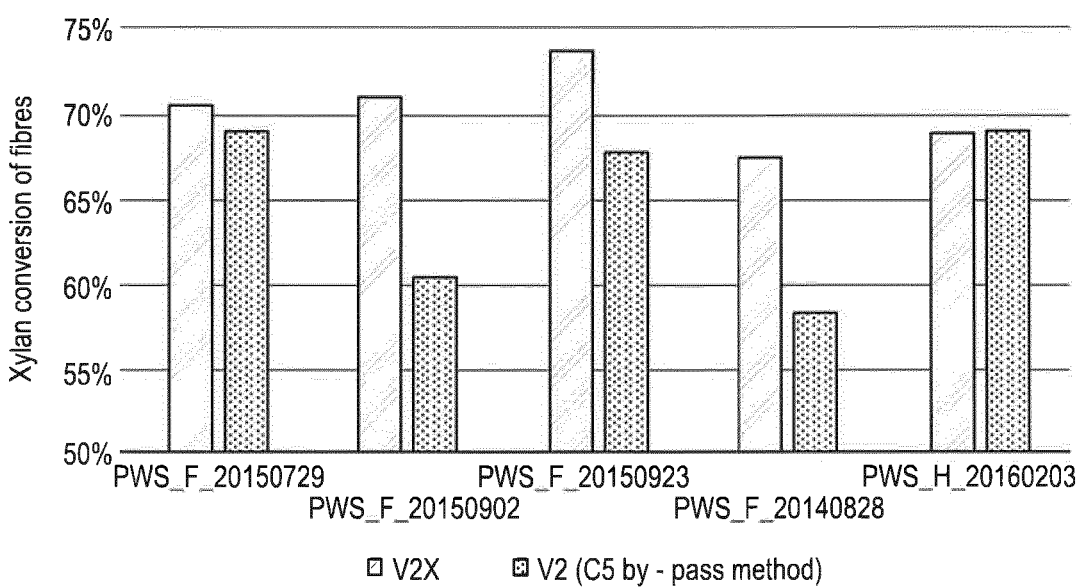
FIG. 10: Xylan conversion of fibers for Version 2.X and the C5 by-pass method for five different pretreatment dates.

At the end of the hydrolysis, the sugar concentrations in all streams were measured and mass balances were set up. The glucan and xylan conversions of the fibers from pre-treatment were calculated based on monomeric sugar concentrations in the fiber slurry (C5 by-pass method) or as sum of the filtrate and fiber cake slurry. Glucan and xylan conversions are shown in FIGS. 9 and 10.

Conclusion

The hydrolysis yield of fibers after pretreatment has been compared for two different wheat straw batches and five different pretreatment dates. In all the trials a significantly better glucan conversion, 13% (relatively) more in V2.X compared to V2, of the fibers has been achieved by performing two stage hydrolysis (V2.X). The xylan conversion showed in most cases also an improved performance with two-stage hydrolysis (V2.X), giving a mean increase of 8% (relatively) more xylose from V2.x compared to V2.

The conclusion is that V2.X is yielding higher than the C5 by-pass (V2) method over a series of experiments with varied biomass composition and repeated pretreatment experiments with approx. 500 kg pretreated wheat straw processed in each experiment.

Example 3—Comparison of Two-Stage Hydrolysis with Enzyme Dose Split

In practical experiments it has been proven that two-stage hydrolysis yields are higher than single stage hydrolysis yields, but the effect is not high if all enzyme is added in the fiber hydrolysis. A significant higher yield is obtained with two stage hydrolysis, when the enzyme dose is split to both stages.

Three fiber hydrolyses were conducted in the free fall reactor in 10 kg scale, one with 50 g CTec3/kg glucan and 22 wt % SS and another two with standard 75 g CTec3/kg glucan; one with 22 wt-% SS and another with 18 wt % SS corresponding to the final dry matter of a two-stage hydrolysis with 22 wt % SS in both fiber hydrolysis and fiber cake hydrolysis. Otherwise standard hydrolysis conditions.

After 44 hours of fiber hydrolysis, the slurries was pressed into a filtrate and a fiber cake as previously described. The fiber cake was re-suspended in water to 22% SS in shake flasks. For the chamber with 50 g CTec3/kg glucan in the fiber hydrolysis, the rest of the enzyme up to a total enzyme dose of 75 g CTec3/kg original glucan was added to the fiber cake hydrolysis. No enzymes were added to the fiber cake for the trial with 75 g CTec3/kg glucan in the fiber hydrolysis.

Results

Figure 11:
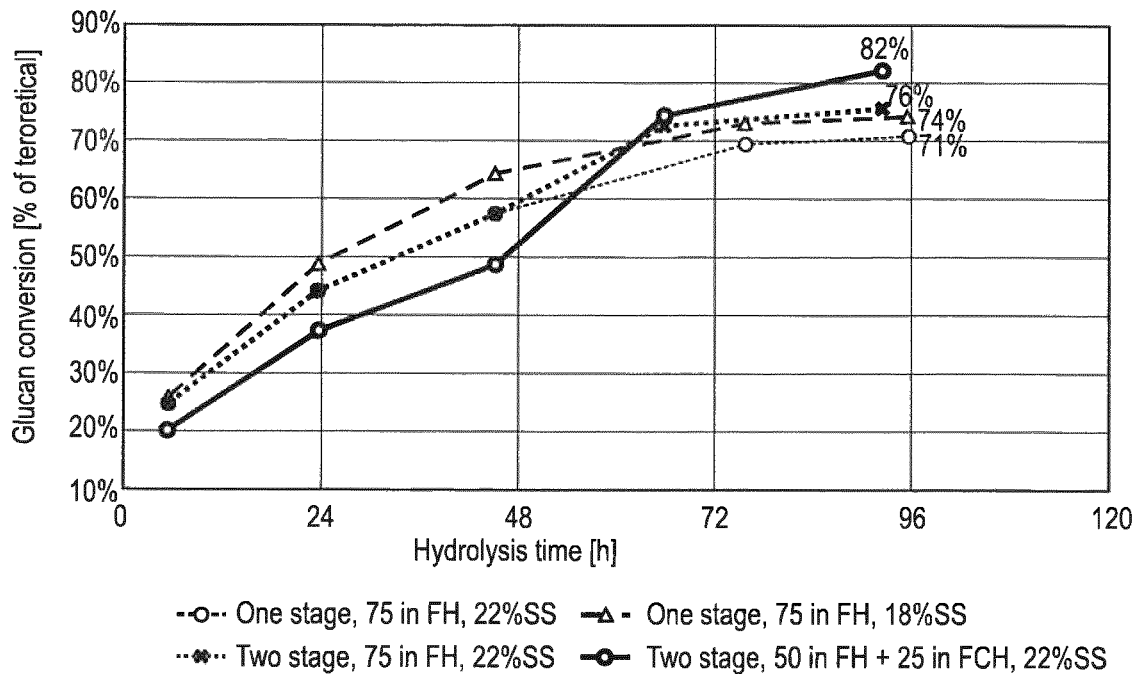
FIG. 11: Total Glucan conversion: Grey circle—One stage hydrolysis with 75 g Cellic® CTec3/kg glucan added in the fiber hydrolysis (FH) and 22 wt-% SS, Dark grey triangle—One stage hydrolysis with 75 g Cellic® CTec3/kg glucan added in the fiber hydrolysis (FH) and 18 wt-% SS, Light grey cross—Two stage hydrolysis with 75 g Cellic® CTec3/kg glucan added in the fiber hydrolysis (FH) and 22 wt-% SS in the fiber hydrolysis and 22 wt-% SS in the fiber cake hydrolysis, and Black un-filled circle—Two stage hydrolysis with 50 g Cellic® CTec3/kg glucan added in the fiber hydrolysis (FH) and 22 wt-% SS in the fiber hydrolysis and 25 g Cellic® CTec3/kg FH glucan (giving 75 g Cellic® CTec3/kg FH glucan in total) added in the fiber cake hydrolysis (FCH) and 22 wt-% SS in the fiber cake hydrolysis.

FIG. 11 shows the results of one and two stage hydrolysis and dependence of dry matter. The lowest conversion (71%) is obtained conducting one stage hydrolysis at 22% SS. The yield is improved in a one stage hydrolysis to 74% if the SS in the hydrolysis is lowered from 22 to 18 wt-% SS. The water consumption in a 18 wt-% SS one stage hydrolysis equals the water consumption in a 22 wt-% SS two-step hydrolysis (because of the two steps at 22% SS). Therefore it is not unexpected that the yield from a one stage hydrolysis at 18% SS is yielding comparable conversion as a two step hydrolysis at 22 wt-% SS, although a small increase in yield is expected due to lower product inhibition in the fiber cake hydrolysis. The yield increases from 74 to 76% going from a one stage hydrolysis to a two stage hydrolysis when maintaining the same water consumption in the overall process. A significant higher yield is obtained with two stage hydrolysis, when the enzyme dose is split and dosed in both stages. By adding only two thirds of the enzyme to the fiber hydrolysis and the rest (one third) of the enzyme to the fiber cake hydrolysis, the glucan conversion increases from 76% to 82%, see FIG. 11.

Conclusion

Going from one to two stage hydrolysis increased the glucan conversion by 6% (relatively) when maintaining the same water consumption in the process. It is of advantage to add some of the enzyme to the fiber hydrolysis and the rest of the enzyme to the fiber cake hydrolysis. This way of: enzyme dosing will enhance the effect of two-step hydrolysis, giving an increase in glucan conversion of 16% (relatively) rather than only 6% (relatively).

Example 4—Comparison of Mixed Sugar Hydrolysis (MSH) with Fibers (C5 Bypass Method) and without Fibers (V2.X Method)

In the V2.X process, process scheme (3), the MSH is a mixture of sugar juice from the fiber hydrolysis and liquid fraction-1. MSH is mixed in a volume ratio of approximately one part of liquid fraction-1 and two parts of liquid fraction 2. No enzymes are added to the mixed sugar hydrolysis. Enzymes are a part of liquid fraction-2. The enzymes added to the fiber hydrolysis and which stay in solution will follow the liquid fraction-2 after solid liquid separation of the fiber hydrolysis.

Experimental work was set-up to prove if there is a difference in the efficiency of xylo-oligomer conversion in MSH (without fibers) and in MSH including fibers (C5 by-pass process).

Standard fiber hydrolysis was conducted in the free fall reactor in 10 kg scale. After 72 hours of fiber hydrolysis, half of the slurry was pressed and the other part was kept as a slurry. The filtrate (liquid fraction-2) and the slurry were transferred to individual shake flasks and liquid fraction-1 was added to all the shake flasks. The MSH was conducted for 96 hours at standard conditions.

Results

Figure 12:
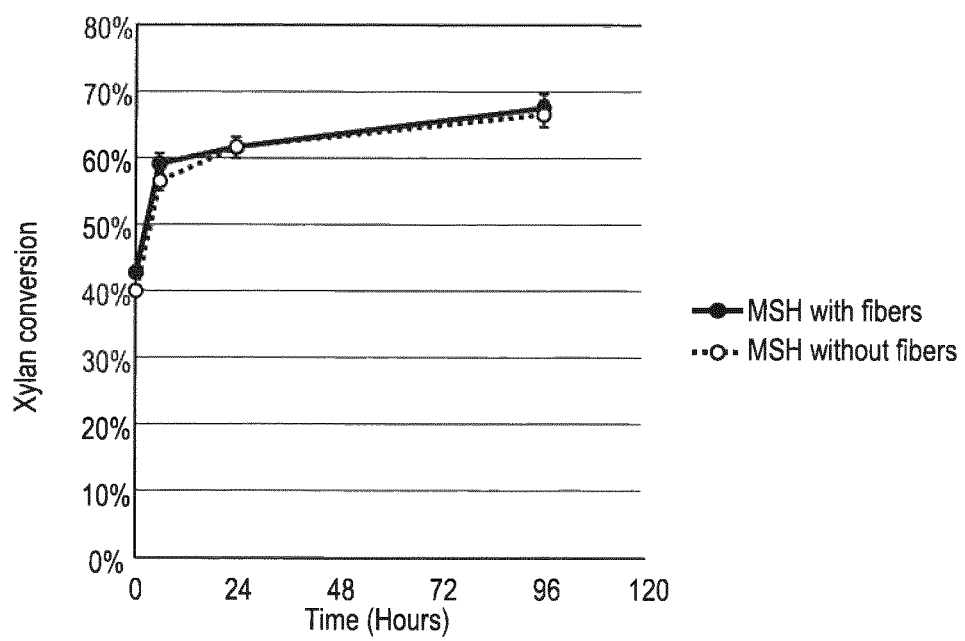
FIG. 12: Xylan conversion in MSH. Colour code dark grey: MSH including fibers; light grey: MSH, where the fibers are removed before addition of C5-bypass.

In FIG. 12, it is seen that the MSH added liquid fraction-1 (without fibers) is giving a similar xylan conversion as the MSH added slurry (with fibers). These data indicate that most of the relevant enzymes (xylanases) in Cellic® Ctec3 are following the filtrate (liquid fraction-2) after fiber hydrolysis.

In the MSH, approximately 40% of the xylan is converted in to monomeric xylose at time zero. Very fast (<10 h) 60% of xylose potential is converted to xylose. After 10 hours, the conversion rate is very slow. At 48 h of MSH, 63-67% of conversion is obtained. By adding high amounts of Cellic® Ctec3, xylan conversion degrees of up to 90% in 48 h were obtained (see e.g. FIG. 13). It is further proven in spiking experiments (data not shown) that monomeric sugars (glucose and xylose) are not inhibiting xylan conversion, but pretreatment inhibitors and oligomer concentration in the mixed sugar hydrolysis have a significant inhibiting effect on xylan conversion.

Conclusion

The MSH is equally efficient with and without fibers, meaning that enzymes important for the hydrolysis of hemicellulose fragments and xylo-oligomers are soluble and following the water phase.

Example 5—Dose Response in Mixed Sugar Hydrolysis

Fiber hydrolysis was conducted in the free fall reactor in 10 kg scale. After 72 hours of fiber hydrolysis, the slurry was pressed. The filtrate (liquid fraction-2) and the liquid fraction-1 was heated to 80° C. for 20 min. to deactivate the enzyme activity. 66 g of the filtrate (liquid fraction-2) from the press was transferred to 12 shake flasks and 33 g liquid fraction-1 was added to all the shake flasks. Different amount of Cellic® CTec3 was added and the MSH was conducted for 48 hours at standard conditions. The concentration in the mixture was measured and the conversion for no enzyme addition in heat-treated liquid was calculated. A MSH with not heated liquids and no enzyme addition was conducted together with the other shake flasks showing the conversion due to enzymes following the filtrate from the fiber hydrolysis.

Results

Figure 13:
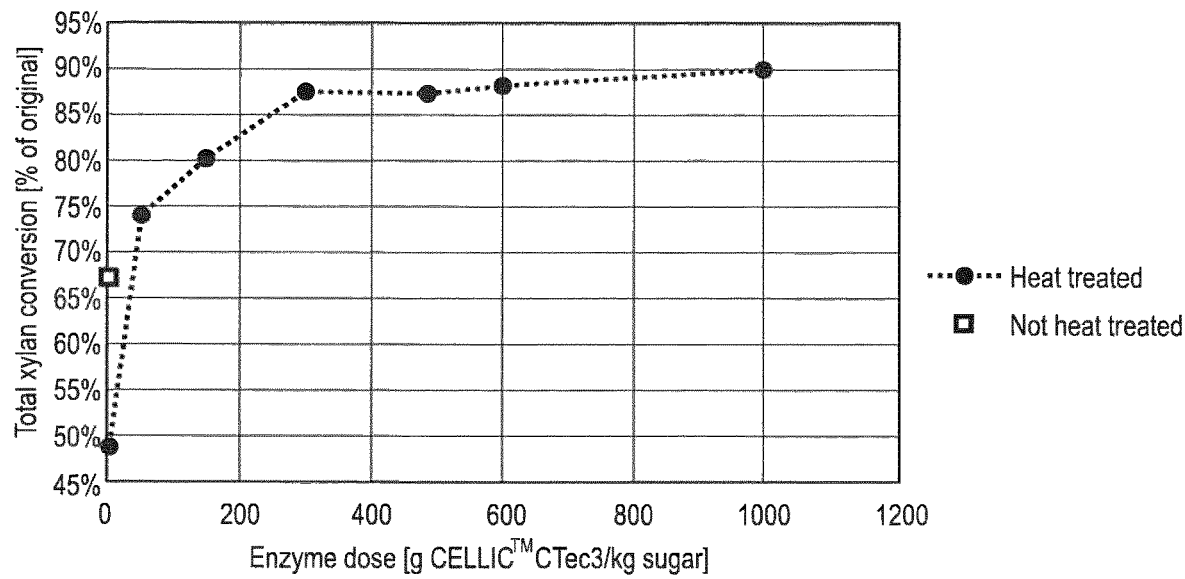
FIG. 13: Total xylan conversion in MSH as function of enzyme dose at 48 hours reaction time (0 hours for heat treated with no enzymes) at pH 5, 250 rpm and 50° C.

FIG. 13 shows the total xylose conversion as a function of enzyme dosage. If all enzyme added to the fiber hydrolysis had been added to the MSH, it would have corresponded to 240 g Cellic® Ctec3/kg sugar. The result without adding active enzyme indicates that only a relatively low part of the enzyme in the filtrate stream is active. Nevertheless, it can also be seen that with a sufficiently high enzyme concentration and hydrolysis time, total xylan conversion of up to 90% can be achieved.

As high enzyme concentration leads to almost complete and/or faster conversion of xylan, recycling of enzymes in MSH could be of great advantage. Ultra-filtration (UF) is a normal unit operation for recovering enzymes from fermentation broth. In this V2.X process, UF could recover enzymes after MSH and recycle them to the MSH. It will lead to high enzyme concentration in MSH over time, which will improve the hydrolysis of xylo-oligomers.

It is also thought that only some enzyme activities are missing due to instability and thus loss of activity during the first 100 hours of reaction or adsorption to the fibers or soluble compounds such as organic degradation products or carbohydrates. Addition of single activities as for example β-xylosidase can thus lead to a great increase in conversion and could be advantageous compared to adding large amounts of enzyme mixtures.

Conclusion

Enzymatic hydrolysis of oligomeric hemicellulose is possible in the liquid fractions from the V2.X process. A conversion of 67% is achieved by hydrolysis of enzymatic activity transferred through the filtrate to the mixed sugar hydrolysis. However, up to 90% could be achieved by adding more enzyme, Cellic® CTec3 or other commercial enzyme mixtures or single activities such as β-xylosidase or others. Increased conversion could also be obtained by recirculating the enzyme for example through up-concentration by ultra-filtration.

Example 6—Addition of β-Xylosidase in MSH

It is believed that addition of β-xylosidase will increase the xylan conversion significantly, such as to at least 80 or 90% in the MSH.

The fiber hydrolysis is conducted in the free fall reactor in 10 kg scale using 75 g CTec3/kg glucan. The slurry is pressed after 72 hours of fiber hydrolysis. Thereafter, 66 g of the filtrate (liquid fraction-2) and 33 g liquid fraction-1 are transferred to 27 shake flasks (three groups in triplicates). In the first group, β-xylosidase is added in a concentration corresponding to 1, 5, 10, 20 and 40% of the "total" enzyme protein added with CTec3 to the fiber hydrolysis. In the second group, CTec3 is added in a concentration corresponding to 10 and 40% of CTec3 added to the fiber hydrolysis. The third group is a control group without extra enzymes addition. The concentration of xylose in the mixture is measured by HPLC and the xylan conversion calculated for each treatment.

The β-xylosidase can e.g. be from *Bacillus pumilus*, such as a high purity recombinant β-xylosidase obtainable from Megazyme (EC 3.2.1.37; CAZy Family: GH43; CAS: 9025-53-0; in 3.2 M ammonium sulphate; supplied at ~75 U/mL, with a specific activity of ~18 U/mg (35° C., pH 7.5 on p-nitrophenyl-β-D-xylopyranoside).

Samples with extra β-xylosidase reveal a significantly higher xylan conversion, such as at least 80 or 90% xylan conversion after MSH, in contrast to the control without enzyme and/or those with CTec3-addition, with a xylan conversion at around 66%.

Example 7—Comparison of Fermentation Substrates from V2 and V2.X Method

The fermentation process in the V2.X process (see e.g. FIGS. 1 and 4) differs from the fermentation process in the C5 by-pass process (V2), process scheme (2) (see e.g. FIG. 3), inter alia, in the way that the fermentation is fed from more than one substrate (hydrolysate from fiber cake hydrolysis and mixed sugar hydrolysis). Furthermore, the fiber cake hydrolysate (Slurry C6+C5 product can be subjected to a further solid/liquid separation step. In the C5 by-pass process there is only one substrate (see FIG. 3) and the fermentation needs dilution with water in the start of the fed batch due to high concentrations of acetic acid and other yeast inhibiting substances as furfural. Otherwise, the time needed for e.g. sugar to ethanol conversion would be prolonged significantly. The composition of the hydrolysates for fermentation in the V2.X process can be seen in Table 8.

TABLE 8

Composition of hydrolysates from mixed sugar hydrolysis MSH and fiber cake hydrolysis (see e.g. FIG. 1, steps (e), and step (f), respectively).

|  | Hydrolysate from step f) [g/kg wet] | Hydrolysate from step e) |
| --- | --- | --- |
| Glucose | 97 | 57 |
| Xylose | 20 | 44 |
| Acetic acid | 2.3 | 9.7 |
| Furfural | 0.3 | 1.2 |
| 5-HMF | 0.1 | 0.3 |

5-HMF: 5-(hydroxymethyl)furfural

As can be seen from Table 8, the hydrolysate from step (f) (hydrolysate-1) contains significantly lower inhibitor concentrations (acetic acid, furfural and 5-HMF) than the hydrolysate from step (e) (hydrolysate-2).

Surprisingly and unexpectedly, the inventors have realised that the two hydrolysates with different inhibitor concentration can be used in a novel and advantageous fermentation process.

Commonly, at the beginning of a fermentation, the hydrolysate is diluted with water in order to reduce the inhibitor concentration to an acceptable level. According to the present invention, a hydrolysate, which is low in inhibitor—e.g. the Slurry C5/C6 product or the liquid C5/C6 product obtained after a solid liquid separation of said Slurry C5/C6 product-, can be used in an initial phase of a microbial fermentation, usually a batch fermentation. In this way, dilution water can be avoided or reduced (if some dilution is still necessary), fermentation time can be reduced, and production costs can be reduced, as less water needs to be removed from the fermentation product, apart from the afore-mentioned timesavings. It is also conceivable that a faster fermentation, as provided e.g. according to the present invention, will reduce the risk of contaminations, i.e. growth of undesired microorganisms, resulting in lower fermentation product yields.

When performing a fermentation, a fed batch set-up may provide one or more of the following benefits:

(1) Furan and/or other inhibitory compounds inhibit different microorganisms including yeast, and consequently, these need to be controlled and/or reduced to a suitable low level to improve growth and/or fermentation product formation, such as yeast growth and EtOH production. When using a fed-batch phase approach this can be achieved, as yeast removes e.g. furans present in the initial batch phase. During the fed batch phase yeast continuously removes furans, so the detected level is very low or even close to zero.

(2) Acetic acid is another inhibitor, and by choosing an initial batch phase with a low level, the production strain will have an easier start, beginning to grow and produce product faster.

(3) In fed batch it is possible to control the feed addition so that the concentration of glucose is kept below approx. 10 g/kg wet, improving the conversion of xylose in C5 GMO yeast.

In all cases, it may also be important to choose the optimal start volume in the initial batch phase compared to the total volume, and an optimal (small) amount of yeast inoculum.

An advantage of having two hydrolysate qualities in term of inhibitor concentration, as in Version 2.X is, that it is possible to conduct fed batch fermentations without dilution in the initial batch phase, while still being able to convert essentially all xylose added in a suitable time frame, even at a very high acetic acid concentration (such as of app. 10 g/kg), and also with a relatively high overall furfural concentration (such as around 1 g/kg wet hydrolysate).

Example 8—Improved Fermentation in V2 Process

Figure 3:
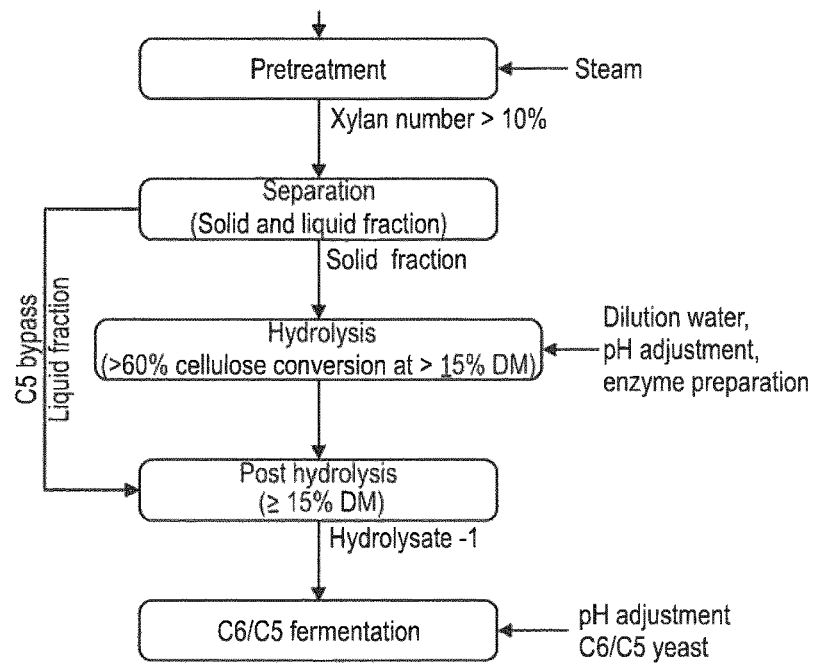
FIG. 3: Process scheme (2) depicts a more complex process scheme comprising a "C5 bypass", also termed "V2" herein, such as processes described in WO 2014/019589.

For a fermentation in the V2 process, all C5 bypass liquid is added to the "post hydrolysis", thereby providing only a single substrate for fermentation (see e.g. Figure. 3). Terms related to "post hydrolysis" used in some examples are believed to be corresponding to mixed sugar hydrolysis (MSH). Likewise, terms related to "C5 bypass" or "C5 bypass liquid faction" are believed to be corresponding to "liquid fraction 1" or "first liquid fraction". Commonly, it is necessary to dilute the post hydrolysis substrate with water in the "initial batch phase" of a fed batch fermentation, in order to reduce the concentration of inhibitors, such as to provide an efficient and/or reliable fermentation, such as in terms of growth of microorganism and/or fermentation product yield. Usually, fermentations are yeast fermentations, aiming at production of 2G EtOH, however, it is believed that other microorganisms can be used as well, thus also providing different fermentation products.

Figure 14:
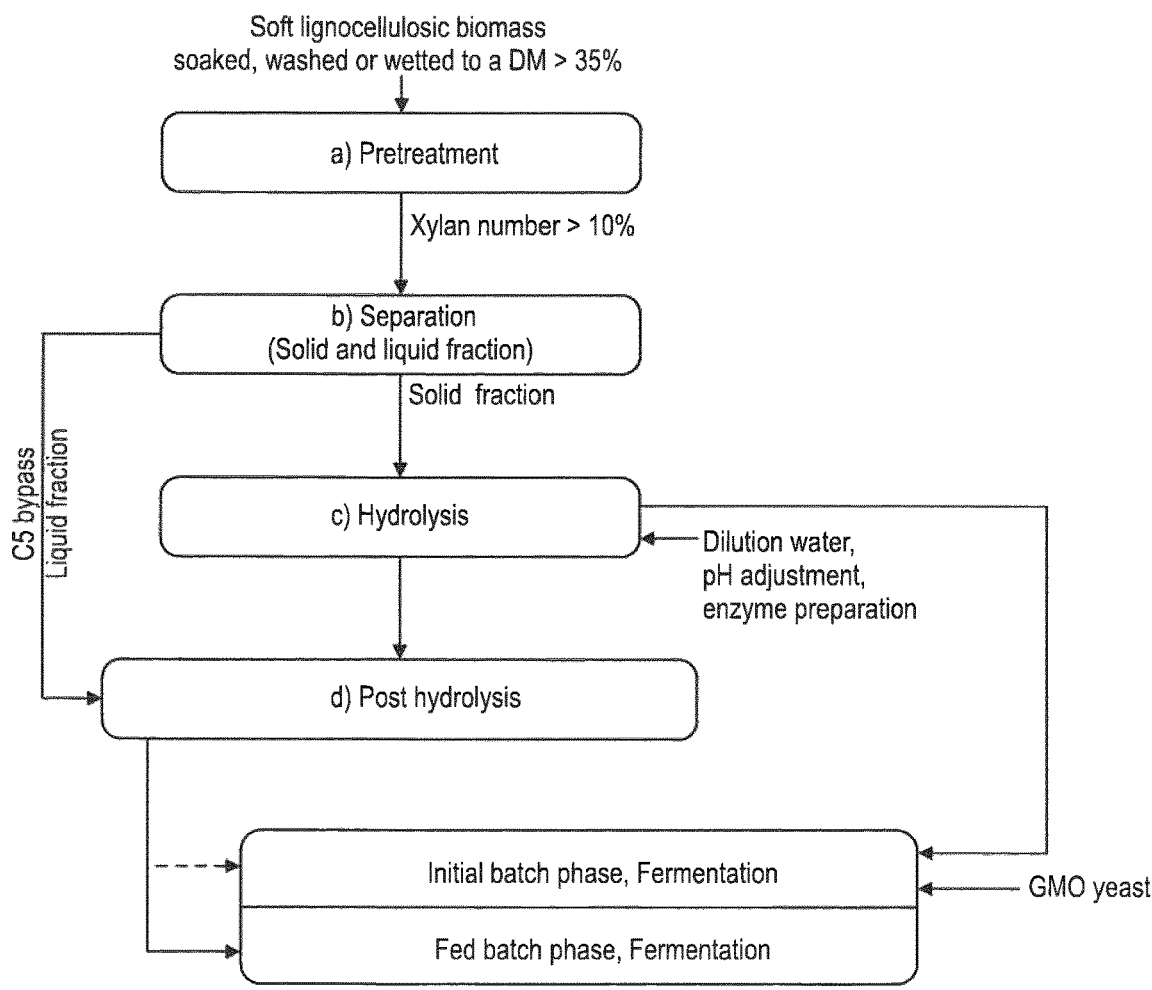
FIG. 14: Embodiment of a V2 setup with improved fermentation.
Figure 15:
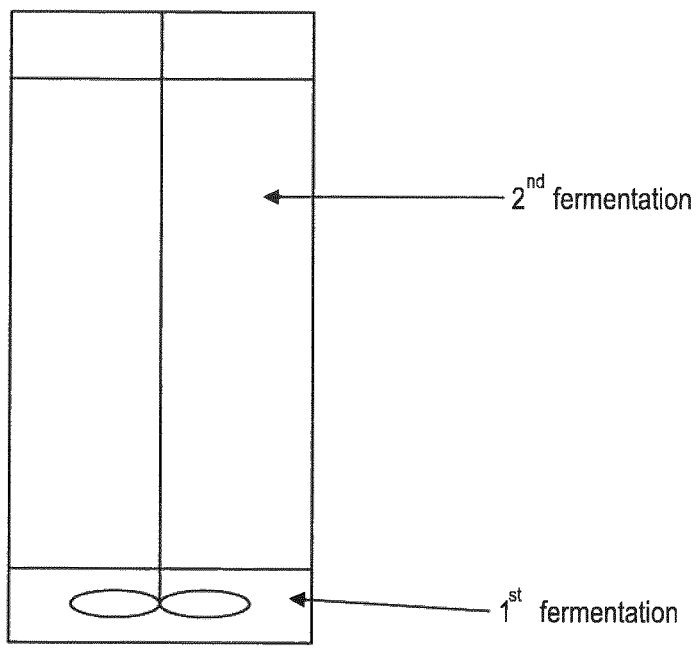
FIG. 15: Schematic outline of a two-step fermentation.

Surprisingly and unexpectedly, the inventors have realised that also the V2 process may be adapted in view of the above findings related to the hydrolysates or product streams with different inhibitor concentrations. See FIG. 14 for an example of a principal set-up of a process for such an improved fermentation. Consequently, in order to avoid (or reduce) dilution in the start of fermentation, it is believed to be possible to use the hydrolysate from the first hydrolysis (e.g. from step (c)), as the material to start the fermentation. This hydrolysate is much lower in yeast inhibitor concentration than the Post Hydrolysate. Once the amount of hydrolysate from step (c) which is needed for the initial batch phase of the fermentation has been removed, the remaining hydrolysate can be mixed with C5 bypass liquid fraction to ensure hydrolysis of C5 oligomers present in C5 liquid. The post hydrolysis step will then have a smaller fraction of hydrolysate from step (c), compared to C5 liquid than in the original set-up. The GMO yeast indicated in FIG. 14 is optional, other suitable microorganisms could be used as well, thus also allowing for provision of other fermentation products than e.g. alcohol/EtOH. Furthermore, it is believed that such a process will work reliable with different DM concentrations, and different xylan numbers. A scheme of a two-step fermentation is seen in FIG. 15. An initial fermentation is conducted using only a fraction, such as e.g.

around 5%, 10% or 20% of the fermenter volume, followed by second fermentation, whereby the fermenter is filled. The first fermentation can e.g. be a batch fermentation, and the second fermentation a fed-batch fermentation.

Figure 16:
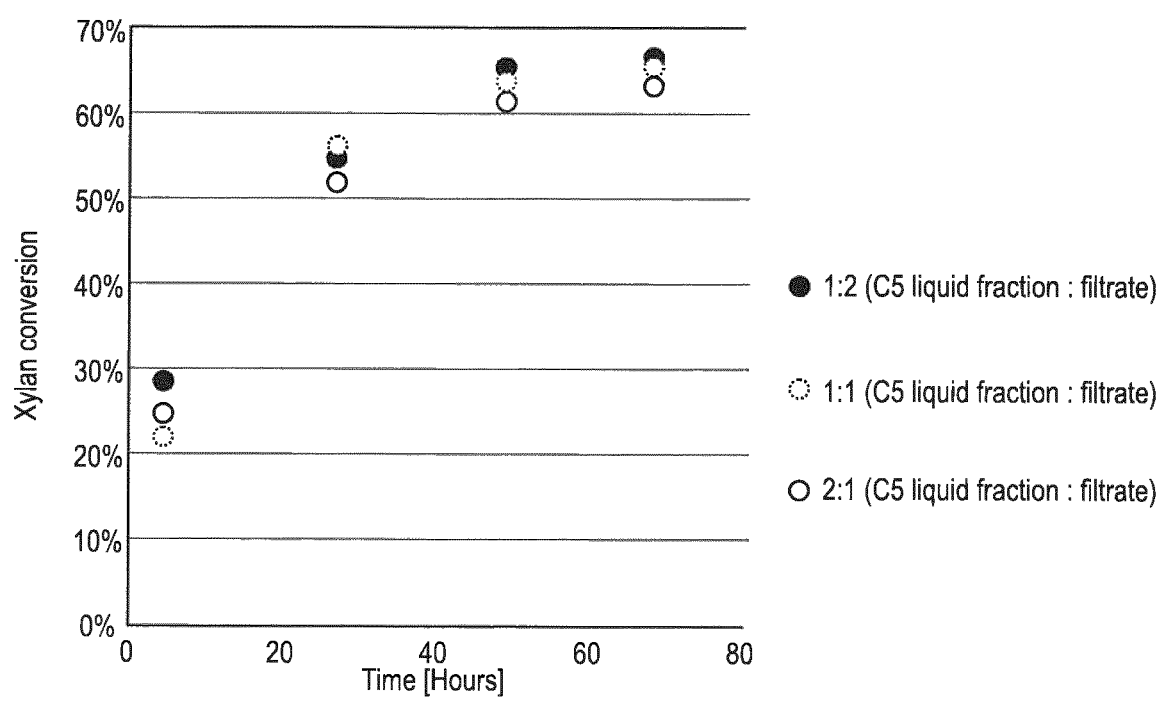
FIG. 16: Changes in xylan conversion at increasing proportions of C5 liquid in the post hydrolysis. "Filtrate" may refer to the liquid fraction after a hydrolysis step, such as hydrolysis step (c) in FIG. 14.

The proportion between C5 liquid fraction and hydrolysate from step (c) will be higher in the post hydrolysis (see FIG. 3) in the proposed improved V2 process. It has been tested, if the hydrolysis in step (d) would be negatively affected. Below is a description of how this was tested, and that the hydrolysis is not negatively affected. Results are shown in FIG. 16.

Materials and Methods

The fiber hydrolysis (step (c)) were conducted in a vertical pilot reactor in 240 kg scale using 75 g CTec3/kg glucan with a dry matter of 22% suspended solids. After 117 hours of fiber hydrolysis, the slurry was pressed. The filtrate and the C5 liquid fraction was mixed in different ratios 1:2, 1:1 and 2:1 in shake flasks with at total volume of 100 gram. The Post Hydrolysis was conducted in shaking incubators for 48 hours at standard conditions; pH 5.0-5.3; 50° C. The concentration of xylose in the mixture was measured by HPLC and the xylan conversion of C5 liquid fraction was calculated for each ratio. To calculate the xylan conversion of C5 liquid fraction, it was assumed that the filtrate from hydrolysis step (c) did not contribute to the increase in xylose concentration as a function of time. FIG. 16 shows changes in xylan conversion at increasing proportions of C5 liquid in the post hydrolysis. Filtrate is the liquid fraction after the hydrolysis step (c). Only very limited effects on hydrolysis efficiency are seen in FIG. 16 (blending 1:1 is a far higher proportion of C5 liquid than would be the case for the improved fermentation setup).

LIST OF REFERENCES

1. Kristensen, J. B., C. Felby, and H. Jørgensen, Determining Yields in High Solids Enzymatic Hydrolysis of Biomass. Appl. Biochem. Biotechnol., 2009. 156: p. 557-562.
2. Petersen, M. Ø., J. Larsen, and M. H. Thomsen, Optimization of hydrothermal pretreatment of wheat straw for production of bioethanol at low water consumption without addition of chemicals. Biomass and Bioenergy, 2009. 33: p. 834-840.
3. Weiss, N. D., et al., A Simplified Method for the Measurement of Insoluble Solids in Pretreated Biomass Slurries. Appl. Biochem. Biotechnol., 2009. 162(4): p. 975-987.
4. Sluiter, A., et al., Determination of Structural Carbohydrates and Lignin in Biomass (NREL/TP-510-42618). 2008, revised August 2012, National Renewable Energy Laboratory.
5. Sluiter, A., et al., Determination of Sugars, Byproducts, and Degradation Products in Liquid Fraction Process Samples. 2005, NREL-Biomass Program.
6. Faulds and Williamson, Appl. Microbiol. Biotechnol. 1995 November; 43(6): 1082-7)
7. Sørensen et al. (2005) "Efficiencies of designed enzyme combinations in releasing arabinose and xylose from wheat arabinoxylan in an industrial fermentation residue" (Enzyme and Microbial Technology 36 (2005) 773-784)
8. Nishitani, K.; Nevins, D. J. (1988). "Enzymatic analysis of feruloylated arabinoxylans (Feraxan) derived from *Zea mays* cell walls. I. Purification of novel enzymes capable of dissociating Feraxan fragments from *Zea mays* coleoptile cell wall". Plant Physiol. 87:883-890.)
9. Rasmussen (2016) "Carbohydrate degradation mechanisms and compounds from pretreated biomass" PHD Thesis, Technical University of Denmark.

The invention claimed is:

1. A method for providing a C5/C6 product from a lignocellulosic material, comprising the steps of:
   a. Autohydrolysis pretreatment of the lignocellulosic material;
   b Solid/liquid separation of the pretreated lignocellulosic material from step (a) into a first solid fraction and a first liquid fraction;
   c. Enzymatic fiber hydrolysis of said first solid fraction from step (b) by use of an enzyme composition capable of degrading lignocellulosic material, thereby providing a C5/C6 fiber slurry comprising C5 and/or C6 sugars;
   d. Solid/liquid separation of at least a portion of the C5/C6 fiber slurry from step (c) into a second solid fraction and a second liquid fraction; and
   e. Combining at least a portion of said first liquid fraction and at least a portion of said second liquid fraction for enzymatic mixed sugar hydrolysis (MSH), whereby a MSH C5/C6 product is provided,
wherein xylose yield of the MSH C5/C6 product from step (e) is at least 60% of theoretical xylose yield.

2. The method according to claim 1, wherein the pretreatment is conducted:
   a. at a dry matter (DM) content in the range of 5-80%, or at a DM content of 10%, 15%, 20%, 25%, 30%, 35%, 40%, 45%, 50%, 55%, 60%, 65%, 70%, 75%, or 80% or at a DM content of more than 80%; and/or
   b. at conditions providing a xylan number of >10% or 6-10%.

3. The method according to claim 1, wherein the enzymatic fiber hydrolysis and/or MSH is/are conducted:
   a. for a period of at least 6 h, 12 h, 24 h, 48 h, or 72 h, or at 12 h, 24 h, 48 h, 72 h, 96 h, or 120 h; and/or
   b. at a pH in the range of at least pH 3.0, and/or at a pH of 4.2, 4.5, 4.7, 4.8, 4.9, 5.0, 5.1, 5.2, 5.3 or 5.4; and/or
   c. at a temperature in the range of 30-70° C. and/or at 40° C., 42° C., 44° C., 46° C., 48° C., 50° C., 52° C., 54° C., 56° C., 58° C., 60° C., 62° C., 64° C., 66° C., 68° C., or 70° C.; and/or a DM content of at least 10%, and/or at a DM content of 15%, 20%, 25%, 30%, 35%, or 40%.

4. The method according to claim 1, wherein the enzyme composition capable of degrading lignocellulosic material comprises:
   a. a cellulase and/or a hemicellulase; and/or
   b. a mixture of cellulase(s) and/or hemicellulase(s); and/or
   c. one or more of xylanase(s), xylosidase(s), arabinoxylanase(s), xyloglucanase(s), glucoronoxylanase(s), glucomannanase(s), esterase(s) and any combination thereof; and wherein the esterase(s) comprise one or more acetylesterases and/or feroyl esterases; and/or one or more of endocellulase(s), endoglucanase(s), exocellulase(s), exoglucanase(s), endoxylanase(s), acetyl xylan esterase(s), xylosidase(s), β-glucosidase(s) and any combination thereof.

5. The method according to claim 4, wherein hemicellulase(s) is/are also present in step (e); and wherein the hemicellulase(s) present in step (e) comprise(s) xylanase(s), xylosidase(s), arabinoxylanase(s), xyloglucanase(s), glucoronoxylanase(s), glucomannanase(s), esterase(s), acetylesterases, feroyl esterase(s), or any combination thereof.

6. The method according to claim 5, wherein all or at least a fraction of the hemicellulase(s) present in step (e) has been added in step (c); and/or one or more hemicellulase(s) is/are added in step (e); and/or wherein one or more additional enzyme(s) are added in step (e), and wherein the additional enzyme(s) are essentially not present in the enzyme composition capable of degrading lignocellulosic material added in step (c); and/or the additional enzyme(s) is one or more of: hemicellulase(s), xylanase(s), xylosidase(s), arabinoxylanase(s), xyloglucanase(s), glucoronoxylanase(s), glucomannanase(s), esterase(s), acetylesterases, feroyl esterase(s), and any combination thereof.

7. The method according to claim 1, wherein step (e) is conducted by combining at least a portion of said first liquid fraction and at least a portion of said second liquid fraction and enzymatically hydrolysing the mixture.

8. The method according to claim 1, wherein step (e) comprises an ultrafiltration step (j) for recycling enzymes present after MSH.

9. The method according to claim 1, wherein the MSH is performed without addition of one or more enzyme(s).

10. The method according to claim 1, wherein
   a. the second liquid fraction possesses a lower fermentation inhibitor concentration than the first liquid fraction; and/or
   b. the second liquid fraction possesses a lower fermentation inhibitor concentration than the MSH C5/C6 product.

11. The method according to claim 1, further comprising a lignin recovery step and wherein said lignin recovery is conducted on the second solid fraction provided in step (d) or (g).

12. The method according to claim 1, wherein the method further comprises
   k. Combining at least a portion of the MSH C5/C6 product with at least a portion of the second liquid fraction from step (d) to obtain a combined C5/C6 product.

13. The method according to claim 12, wherein the combined C5/C6 product consists essentially of the MSH C5/C6 product from step (e) and the second liquid fraction from step (d).

14. The method according to claim 13, wherein said method further comprises the steps of:
   m. Providing a C5/C6 product for fermentation by combining at least a portion of one or more of:
      (i) the first liquid fraction from step (b);
      (ii) the C5/C6 fiber slurry from step (c);
      (iii) the second liquid fraction from step (d);
      (iv) the MSH C5/C6 product from step (e); and
      (v) the combined C5/C6 product from step (k); and
   n. Fermentation of said C5/C6 product with a microorganism to provide a fermentation product.

15. The method according to claim 14, wherein the fermentation product is provided in a fermentation broth, wherein said method further comprising the step(s) of:
   o. Recovering said fermentation product from the fermentation broth; and/or
   p. Recovering lignin from a spent fermentation broth, and/or from at least a portion of the fermentation product provided from step (n) or (o).

16. The method according to claim 14, wherein the fermentation is carried out in at least a first and a second fermentation step, wherein a first and a second fermentation substrate are fermented.

17. The method according to claim 1, wherein glucose yield of the C5/C6 fiber slurry from step (c) is at least 60% of theoretical glucose yield.

18. The method according to claim 1, wherein the method further comprises
   f. Enzymatic fiber cake hydrolysis of said second solid fraction from step (d) to obtain a slurry C5/C6 product, wherein xylose yield of the C5/C6 fiber slurry from step (c) and/or the slurry C5/C6 product from step (f) is at least 60% of theoretical xylose yield.

* * * * *